United States Patent
Patel et al.

(10) Patent No.: US 10,875,002 B2
(45) Date of Patent: Dec. 29, 2020

(54) ISOTHERMAL REACTOR

(71) Applicant: COMMONWEALTH SCIENTIFIC AND INDUSTRIAL RESEARCH ORGANISATION, Acton (AU)

(72) Inventors: Jim Patel, Acton (AU); Tejas Bhatelia, Acton (AU); Pranab Rakshit, Acton (AU); Paul Webley, Acton (AU); Ravi Kumar Voolapalli, Acton (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 0 days.

(21) Appl. No.: 16/484,500

(22) PCT Filed: Feb. 8, 2018

(86) PCT No.: PCT/AU2018/050097
§ 371 (c)(1),
(2) Date: Aug. 8, 2019

(87) PCT Pub. No.: WO2018/145160
PCT Pub. Date: Aug. 16, 2018

(65) Prior Publication Data
US 2020/0030765 A1 Jan. 30, 2020

(30) Foreign Application Priority Data
Feb. 8, 2017 (AU) .................. 2017900382

(51) Int. Cl.
*B01J 8/04* (2006.01)
*B01J 8/02* (2006.01)

(52) U.S. Cl.
CPC ........... *B01J 8/0496* (2013.01); *B01J 8/0292* (2013.01); *B01J 8/0453* (2013.01); *B01J 2208/00132* (2013.01)

(58) Field of Classification Search
CPC . B01J 8/065; B01J 8/067; B01J 8/0492; B01J 8/0496; B01J 8/0453; B01J 2208/065; B01J 2208/00132
See application file for complete search history.

(56) References Cited

U.S. PATENT DOCUMENTS

| 3,970,435 A | 7/1976 | Schultz et al. |
| 4,338,475 A | 7/1982 | Pennington et al. |

(Continued)

FOREIGN PATENT DOCUMENTS

| EP | 0 386 692 | 9/1990 |
| JP | 11-80052 | 3/1999 |

(Continued)

OTHER PUBLICATIONS

Tejas Bhatelia et al., "CFD Modelling of a Tubular Reactor for Methanol Synthesis", APCChE 2015 Congress incorporating Chemeca 2015, Paper No. 3135027, pp. 302-311.

(Continued)

*Primary Examiner* — Lessanework Seifu
(74) *Attorney, Agent, or Firm* — Nixon & Vanderhye P.C.

(57) ABSTRACT

A reactor (1) for thermochemical reactions is provided comprising a reactor shell (13) having an inlet (2) and an outlet (3). Solid catalyst (16) is provided in reaction zones (4a, 4b, 4c) in which at least a portion of reactants entering the reactor (1) undergo a thermochemical reaction. A heat exchange medium is provided in heat exchange zones such that heat is exchanged between the reaction zones (4a, 4b, 4c) and the heat exchange medium. One or more hollow inserts (11) at least partially extend through the reaction zones (4a, 4b, 4c). The hollow inserts (11) are configured to form a flow path to either: divert a portion of the reactants from the reactor inlet (2) or from one reaction zone to a different reaction zone; or divert a portion of the heat (Continued)

exchange medium from one heat exchange zone to a different heat exchange zone.

17 Claims, 13 Drawing Sheets

(56) References Cited

U.S. PATENT DOCUMENTS

| | | | |
|---|---|---|---|
| 4,735,780 A | 4/1988 | Noe | |
| 5,405,586 A | 4/1995 | Koves | |
| 6,069,271 A * | 5/2000 | Tanimoto | B01J 8/067 422/198 |
| 7,132,555 B2 * | 11/2006 | Te Raa | B01J 8/008 549/533 |
| 8,961,909 B2 * | 2/2015 | Lehr | B01J 8/065 422/651 |
| 2004/0096370 A1 | 5/2004 | Blanchard | |
| 2007/0299148 A1 | 12/2007 | Verbist | |

FOREIGN PATENT DOCUMENTS

| | | |
|---|---|---|
| WO | 2003/084655 | 10/2003 |
| WO | 2015/091445 | 6/2015 |

OTHER PUBLICATIONS

Suzana Yusup et al., "A Simulation Study of an Industrial Methanol Reactor Based on Simplified Steady-State Model", IJRRAS, Dec. 2010, vol. 5, No. 3, pp. 213-222.

International Search Report for PCT/AU2018/050097 dated Apr. 24, 2018, 5 pages.

Written Opinion of the ISA for PCT/AU2018/050097 dated Apr. 24, 2018, 5 pages.

Search Report issued in EP Appln. No. 18751164.7 dated Sep. 21, 2020.

* cited by examiner

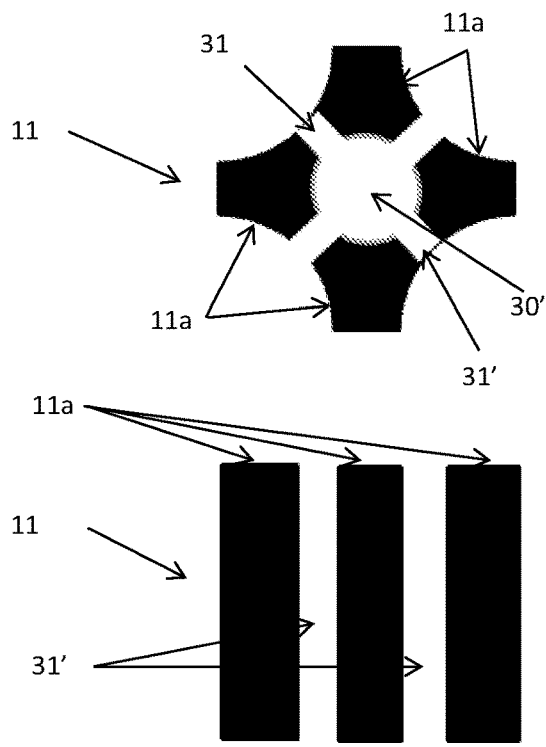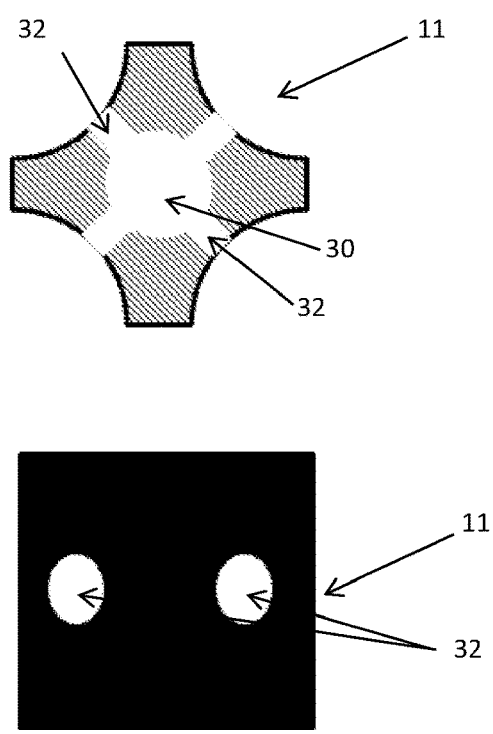
Figure 13a
Figure 13b
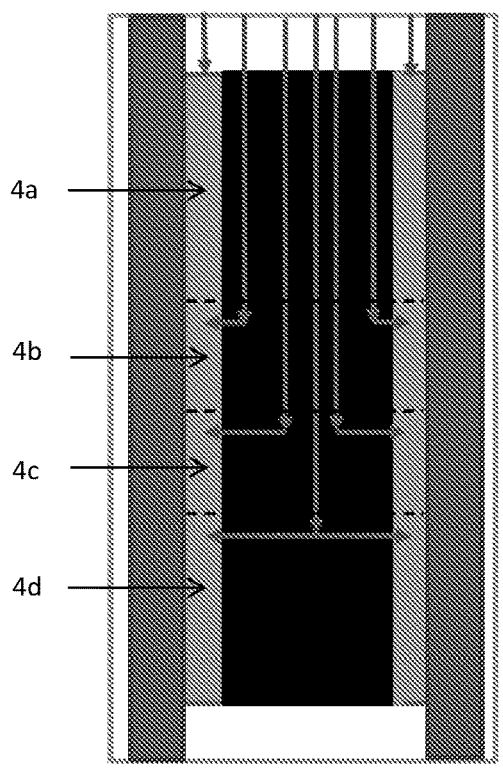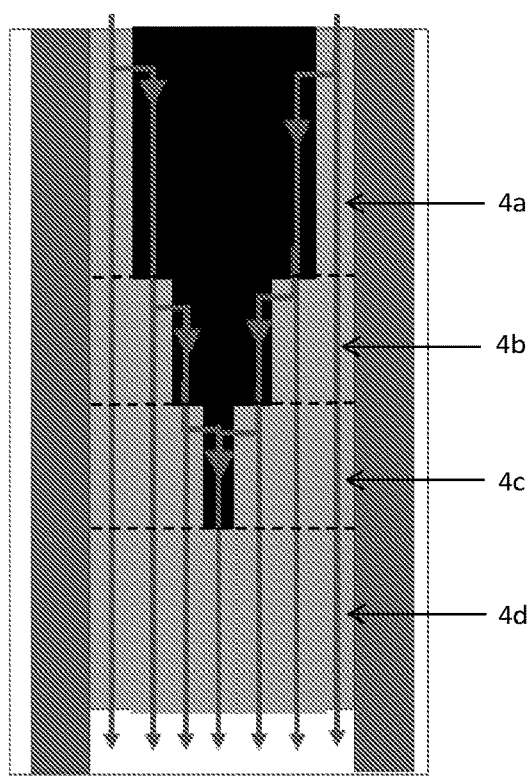
Figure 14a
Figure 14b

ISOTHERMAL REACTOR

TECHNICAL FIELD

The present disclosure relates to catalytic reactors, and more particularly to catalytic reactors for thermochemical reactions. In particular, the present disclosure relates to an apparatus and method for reducing temperature variations and improving the performance of the reactor in which a thermochemical reaction is taking place.

BACKGROUND

Catalytic reactions involve the conversion of one or more reactants to one or more desired products in the presence of a catalyst, for example the reaction between carbon monoxide and hydrogen in the presence of a Cu/ZnO catalyst to produce methanol. Many catalytic reactions are thermochemical reactions, i.e. exothermic in which heat is released during the course of the reaction, or endothermic in which heat is absorbed during the course of the reaction. However, some catalytic reactions are also highly temperature dependent, only operating efficiently in a narrow range of temperatures.

In view of the temperature dependence of some catalytic reactions and their thermochemical nature, catalytic reactions are often conducted in isothermal reactors which aim to keep the temperature of the reactions zones comprising the catalyst as near as possible to an optimal reaction temperature. Isothermal reactors typically comprise a number of heat exchangers to heat or cool the reactants as the reaction proceeds to maintain the temperature in the desired temperature range for the reaction. For example, tube reactors comprising a number of tubes running through the reactor may be used as an isothermal reactor for catalytic reactions.

One example of a tube reactor is a multi-tubular reactor in which the catalyst is contained in a plurality of tubes extending through the reactor. A heat exchange fluid flows through the reactor, heating (or cooling) the reaction tubes as the reaction proceeds. In an alternative configuration, the tube reactor may be a tube-cooled reactor in which the catalyst is placed in the voids between the tubes and the heat exchange fluid flows through the tubes.

Maintaining substantially isothermal conditions within tube-cooled reactors can be difficult, particularly for highly exothermic or endothermic reactions. The temperature of the catalyst in tube-cooled reactors can vary radially, from where the catalyst is in contact with the tubes to where the catalyst is at a distance furthest from the tubes, leading to potential "hot spots" (or "cold spots") whereby the temperature may be outside the optimal range for the reaction. The formation of hot spots (or, conversely, cold spots) can lead to a decrease in efficiency of the tube-cooled reactor, and potentially lead to undesirable secondary reactions occurring at the points furthest away from the tubes. Similarly, in multi-tubular reactors, hot or cold spots may develop along the axis of the tube where the catalyst is at the furthest point from heat transfer effects occurring at the tube wall.

The temperature of the catalyst in tubular reactors can also vary axially. Typically, the thermal energy released or absorbed by the thermochemical reaction will be higher towards the reactor inlet than the thermal energy released or absorbed towards the reactor outlet because the concentration of reactants available to undergo reaction is greater towards the reactor inlet.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

Throughout this specification the word "comprise", or variation such as "comprises" or "comprising", will be understood to imply the inclusion of a stated element, integer or step, or group of elements, integers or steps, but not the exclusion of any element, integer or step, or group of elements, integers or steps.

According to a first aspect, there is provided a reactor for thermochemical reactions, comprising:

a reactor shell having an inlet for receiving reactants into the reactor and an outlet for the removal of products from the reactor;

a plurality of reaction zones comprising a solid catalyst in which at least a portion of the reactants undergo a thermochemical reaction and form a reaction mixture of products and reactants;

a plurality of heat exchange zones comprising a heat exchange medium;

a plurality of tubes for housing the reaction zones or the heat exchange medium, wherein heat is exchanged between the at least one reaction zone and the heat exchange medium through walls of the tubes; and one or more hollow inserts at least partially extending through one or more reaction zones thereby to displace solid catalyst in the reaction zone and reduce temperature variation across the reaction zone, wherein each hollow insert comprises an inlet and an outlet, the hollow inserts configured to either:

form a flow path to divert a portion of the reactants or reaction mixture from the reactor inlet or from one reaction zone to a different reaction zone; or form a flow path to divert a portion of the heat exchange medium from one heat exchange zone to a different heat exchange zone.

According to a second aspect, there is provided a reactor for thermochemical reactions comprising:

a reactor shell having an inlet for receiving reactants into the reactor and an outlet for the removal of products from the reactor;

a plurality of heat exchange tubes positioned in the shell;

at least one reaction zone comprising a solid catalyst located in voids between the heat exchange tubes in which at least a portion of the reactants undergo a thermochemical reaction, wherein heat is exchanged between the at least one reaction zone and the heat exchange tubes; and at least one insert extending at least partially through the at least one reaction zone, thereby to displace solid catalyst in the reaction zone and reduce temperature variation across the at least one reaction zone.

According to a third aspect, there is provided a reactor for thermochemical reactions comprising:

a reactor shell having an inlet for receiving reactants into the reactor and an outlet for the removal of products from the reactor;

a plurality of reaction tubes positioned in the shell, each reaction tube comprising at least one reaction zone comprising a solid catalyst in which at least a portion of the reactants undergo a thermochemical reaction;

a heat exchange medium located in voids between the reaction tubes, wherein heat is exchanged between the at least one reaction zone and the heat exchange medium through walls of the reaction tubes; and at least one insert extending at least partially through the at least one reaction zone, thereby to displace solid catalyst in the reaction zone and reduce temperature variation across the at least one reaction zone.

The reactor of the present invention is able to advantageously avoid "hot or cold spots" within the reaction zone through placing inserts within the reaction zone to regulate heat flow within the reaction zone. In doing so, reactor performance may be enhanced and the amount of required solid catalyst reduced.

In some embodiments, the inserts are solid and preferably have a thermal conductivity greater than the thermal conductivity of the solid catalysts. The inserts are preferably an inert structure which serves to displace a volume of catalyst and assist in regulating temperature within the reactor.

The use of the inserts to divert of portion of heat exchange medium may further assist in regulating the temperature profile within the reactor and enable greater reactor design options to become available.

The use of the inserts to divert a portion of the reactant or reaction mixture stream enables the space velocity profile of the reactor to be controlled. Particularly in gaseous reactions the volume of reaction mixture may change significantly within the reactor and, as such, the ability to regulate the velocity profile within the reactor provides the ability to improve reactor performance.

The tubes are preferably longitudinally extending tubes, although different tube configurations may be used dependent upon the reactor type and configuration. In certain embodiments, the reaction zones are located within the tubes, and the reactor shell is configured to receive a heat exchange medium for exchanging heat with the reaction tubes. In alternative embodiments, the reaction zones are located within the shell, and the plurality of tubes are configured to receive a heat exchange medium for exchanging heat with the reaction zones.

The one or more inserts preferably comprises a central core component and a web member. In some embodiments, at least one insert is connected to one or more tubes with a web member. The web member may comprise a thermally conductive material, preferably having a higher thermal conductivity than the solid catalyst. The web member(s) may extend continuously along the length of the insert. Alternatively, the web member(s) may extend at discrete intervals along the length of the insert(s).

In one embodiment, the heat exchange medium flows through the reactor. The heat exchange medium may flow in a countercurrent or cross flow direction to a flow of the reactants. Alternatively, the heat exchange medium may flow in a co-current direction to the flow of the reactants.

In certain embodiments, at least one said insert extends along an entire length of the at least one reaction zone. In an alternative embodiment, at least one said insert partially extends through the at least one reaction zone. Optionally, a combination of these embodiments may be provided in which some inserts may extend completely through the or each of the reactions zones and other inserts may partially extend through the or each of the reaction zones.

In certain embodiments, a diameter of at least one said insert may be constant along a length of said insert. Alternatively, in other embodiments, the diameter of at least one said insert may vary along the length of said insert. For example, the diameter of at least one said insert may vary continuously along the length of the insert, or the diameter of at least one said insert may vary at discrete intervals along the length of the insert.

The reactor may further comprise one or more wall inserts mounted on an inner wall of the reactor shell.

In certain embodiments, the at least one insert is thermally conductive and preferably has a thermal conductivity of at least 10, more preferably at least 50 and even more preferably at least 100 $W \cdot m^{-1} \cdot K^{-1}$ measured at atmospheric pressure at 293K.

The plurality of reaction zones may be arranged sequentially in the reactor such that the one or more reactants may pass sequentially through the reaction zones.

The reactor may further comprise one or more reaction-free zones. In one embodiment one or more reaction-free zones may be disposed between sequential reaction zones.

The at least one insert may define a flow path between the inlet and a selected reaction zone in an arrangement whereby the reactants received via the inlet may bypass one or more reaction zones and flow directly to the selected reaction zone. The flow path may be defined by at least one longitudinally extending bore in the insert. The flow path may be further defined by at least one laterally extending bore in fluid communication with the selected reaction zone and the at least one longitudinally extending bore. Alternatively, the at least one insert may comprise an assembly of insert portions which, when assembled, define a longitudinally extending passage with one or more laterally extending passages.

The one or more inserts are preferably positioned such that the maximum distance between the solid catalyst and the nearest heat exchange zone is reduced. Preferably, the one or more insert has a diameter sized to sufficiently reduce the maximum distance between the solid catalyst and the nearest heat exchange zone in order to reduce temperature variation across the at least one reaction zone. For example, the one or more insert has a diameter such that the maximum distance between the solid catalyst and the nearest heat exchange zone is reduced by at least 1%, in some embodiments by at least 5% and in further embodiments by at least 10%.

Preferably, the one or more inserts are spaced apart from the heat exchange zones by the solid catalyst such that the amount of catalyst between the inserts and/or heat exchanger zones is kept substantially constant. The density or number of inserts may be substantially constant across each cross-sectional quadrant around a longitudinal axis of the reactor. The at least one said insert may be spaced substantially equidistantly from adjacent heat exchange zones. Preferably, the inserts are disposed in a symmetrical arrangement relative to a longitudinal axis.

In certain embodiments, at least one said insert extends through at least one reaction zone. In an alternative embodiment, at least one said insert partially extends through at least one reaction zone. Optionally, a combination of these embodiments may be provided in which some inserts may extend through the or each of the reactions zones and other inserts may partially extend through the or each of the reaction zones.

In some embodiments, at least one insert is connected to one or more adjacent heat exchangers with a web member.

The reactor is selected from the group consisting of: fixed bed reactors; shell and tube reactors; U-tube reactors; fluidised bed reactors; multiple stage reactors; and dual bed reactors. Preferably, the reactor is a fixed bed reactor.

According to a fourth aspect, there is provided a method of designing a reactor comprising the steps of:

A. generating a thermochemical reactor model for a reactor according to the first, second or third aspects;
B. portioning the reactor into one or more virtual reaction zones along a longitudinal axis of the reactor;
C. using the reactor model to determine an expected temperature across each of the virtual reaction zones $Tvr_i$ to compare against a target temperature $T_{target}$;
D. adjusting one or more of the following parameters:
  i. the number, diameter, length and/or positioning of the one or more inserts;
  ii. the inlet point and the outlet point of the one or more inserts;
  iii the amount of catalyst per unit volume of the reactor;
  iv the location of the catalyst with respect of the heat exchange zone, hollow inserts and/or inserts;
  v space velocity of a reactant/reaction mixture within the reactor to thereby meet or approach the criteria of $Tvr_i$ to equal $T_{target}$;
E. repeating step D until said criteria is satisfied.

The method of designing a reactor according to the present invention enables inserts to be strategically positioned to regulate the thermal profile and/or space velocity profile of the reactor. Armed with the specific chemical reaction being performed and preferably the solid catalyst characteristics, a reactor may be designed for enhanced performance whilst catalyst volumes maybe reduced compared to proprietary reactor systems.

Preferably, the reactor model comprises one of more of the following differential equations:
  reaction kinetics differential equation;
  energy balance differential equation; and/or
  pressure drop differential equation.

Preferably, step D further comprises adjusting number, diameter, length and/or positioning of one or more inserts. The adjusted lengths of inserts and/or hollow inserts preferably correspond to the length of one or more reaction zones. This conveniently enables temperature and/or space velocities to be regulated for each reaction zone.

The reactor may also comprise one or more reaction-free zones.

The target temperature ($T_{target}$) preferably comprises a temperature range ($\Delta T$). The size of the preferred temperature range will be reflected by the specific reactor system. In general, $\Delta T$ should be as small as practical and preferably between 10° C. and 100° C. and more preferably between 20° C. and 50° C.

The one or more reaction and/or reaction-free zones may be virtual reaction or virtual reaction-free zones. That is, for example, the catalyst distribution may be continuous along a section of the reactor, with the section being divided into small subsections, each representing a reaction zone, for the purposes of calculating the placement of number of inserts, including hollow inserts for diverting reactants/reaction mixtures between different zones. Thus, the use of virtual zones are particularly useful in the design process to determine positioning of the inserts, although the virtual zones may or may not result in each virtual reaction or non-reaction zones having a different reactor design configuration.

According to a fifth aspect, there is provided a method of reducing temperature variation across one or more reaction zones in a reactor for thermochemical reactions,
  wherein said reactor comprises:
  a reactor shell having an inlet for receiving reactants into the reactor and an outlet for the removal of products from the reactor;

a plurality of reaction zones comprising a solid catalyst in which at least a portion of the reactants undergo a thermochemical reaction;
a plurality of heat exchange zones comprising a heat exchange medium; and
a plurality of tubes for housing the reaction zones or the heat exchange medium, wherein heat is exchanged between the reaction zones and the heat exchange medium through walls of the tubes,
the method comprising:
introducing one or more hollow inserts at least partially extending through one or more reaction zones thereby to displace solid catalyst in the reaction zone and reduce temperature variation across the reaction zone, each hollow insert comprising an inlet and an outlet, configured to either:
  form a flow path to divert a portion of the reactants or reaction mixture from the reactor inlet or from one reaction zone to a different reaction zone; or
  form a flow path to divert a portion of the heat exchange medium from one heat exchange zone to a different heat exchange zone.

In the above method of reducing temperature variation across one or more reaction zones in a reactor for thermochemical reactions, at least one of the following parameters may be determined using a method according to the fourth aspect:
  i. the number, diameter, length and/or positioning of the one or more inserts;
  ii. the inlet point and the outlet point of the one or more inserts;
  iii the amount of catalyst per unit volume of the reactor;
  iv the location of the catalyst with respect of the heat exchange zone, hollow inserts and/or inserts;
  v space velocity of a reactant/reaction mixture within the reactor In a sixth aspect, there is provided use of a reactor according to the first, second or third aspects of the invention, or designed using the fourth or fifth aspects of the invention, for reacting at least one gaseous reactant. The reactor is preferably used for reacting at least two or even more preferably at least three gaseous reactants.

In one embodiment, the gaseous reactants are components of synthesis gas, including methane, carbon monoxide, carbon dioxide and hydrogen. Preferably, use of the reactor is for producing methanol from synthesis gas, or components thereof including hydrogen and carbon monoxide; or hydrogen and carbon dioxide; or combinations thereof.

In an alternative embodiment, the reactor is used for exothermic methanation reactions such as the hydrogenation of $CO_x$ to form methane or as a step in the creation of syngas. For example, the reactor may be used for the methanation of carbon dioxide according to equation 1:

$$CO_2 + 4H_2 \rightarrow CH_4 + 2H_2O \qquad (1)$$

In a further embodiment, the reactor may produce Fischer Tropsch (FT) products from synthesis gas or components thereof. FT products preferably include hydrocarbon products comprising at least four carbon atoms and more preferably hydrocarbon products which are liquid at room temperature and pressure. The FT reaction preferably produces alkanes according to the equation 2, with n preferably being between 10 and 20.

$$(2n+1)H_2 + n\,CO \rightarrow C_nH_{2n+2} + n\,H_2O \qquad (2)$$

It will be appreciated that the reactor described herein is not limited to the above described uses, but may be used to reduce temperature variations for any number of catalytic, thermochemical reactions involving gaseous reactants and products. By way of non-limiting examples, in addition to the above examples, the reactor described herein may also be used for dimethyl ether (DME) synthesis (e.g. from syngas), ammonia synthesis, hydrogenation reactions, and hydrocarbon reforming processes.

Accordingly, in a seventh aspect, there is provided a method of reacting at least one gaseous reactant in a thermochemical reaction, the method comprising passing the at least one gaseous reactant through a reactor according to any one of the first, second or third aspects, wherein at least a portion of the gaseous reactant undergoes a thermochemical reaction in the reactions zones, and wherein one or more inserts at least partially extends through one or more reaction zones thereby to displace solid catalyst in the reaction zone and reduce temperature variation across the reaction zones.

BRIEF DESCRIPTION OF DRAWINGS

Embodiments of the present disclosure will now be described, by way of example only, with reference to the accompanying drawings in which:

FIGS. 13a and 13b are a cross-sectional and longitudinal views of inserts according to yet further alternative embodiments of the present disclosure;

FIGS. 14a and 14b are schematic cutaway side views of reactors according to still further alternative embodiments of the present disclosure

DESCRIPTION OF EMBODIMENTS

Figure 1:
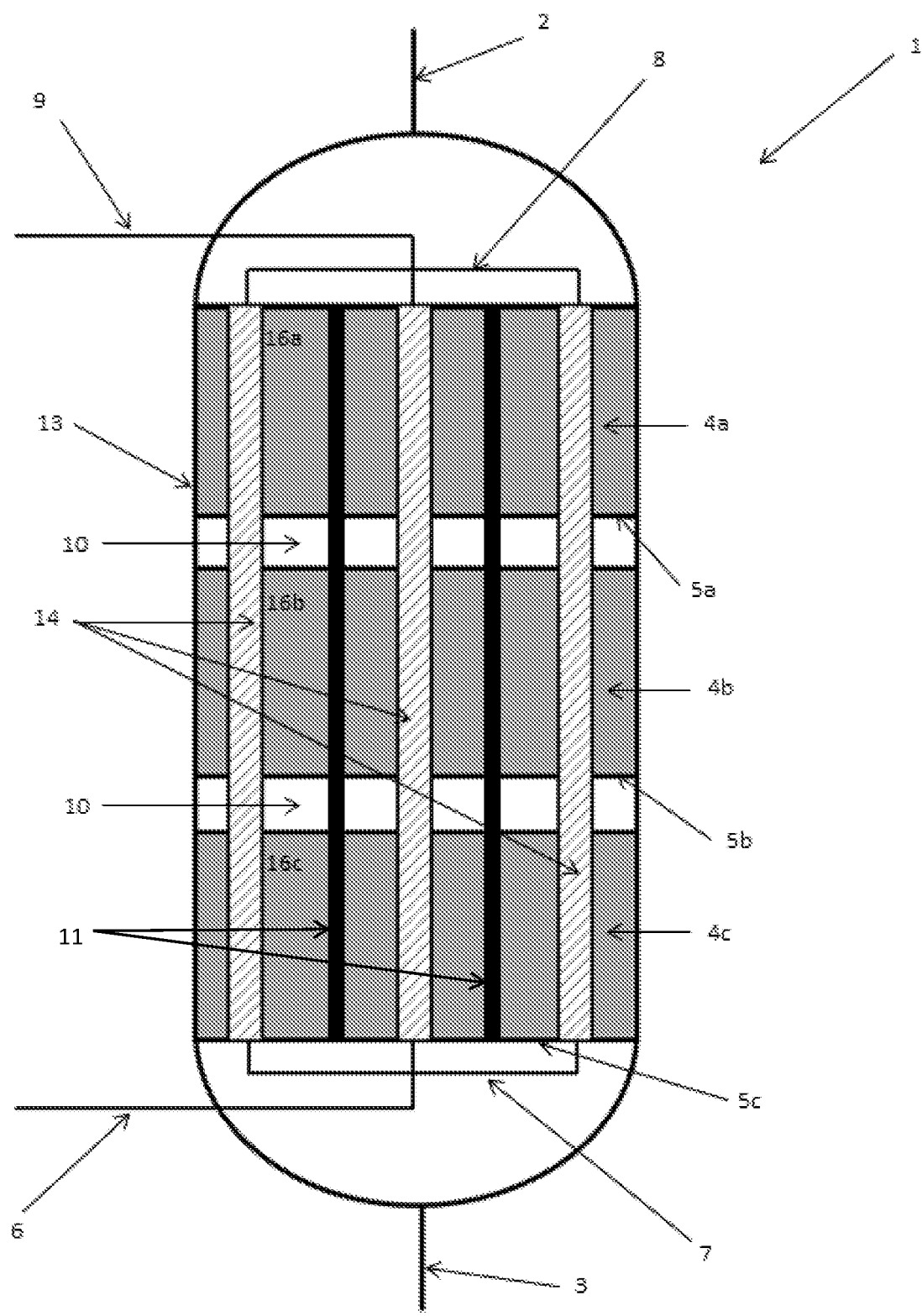
FIG. 1 is a schematic cutaway side view of a reactor according to an embodiment of the present disclosure.
Figure 2:
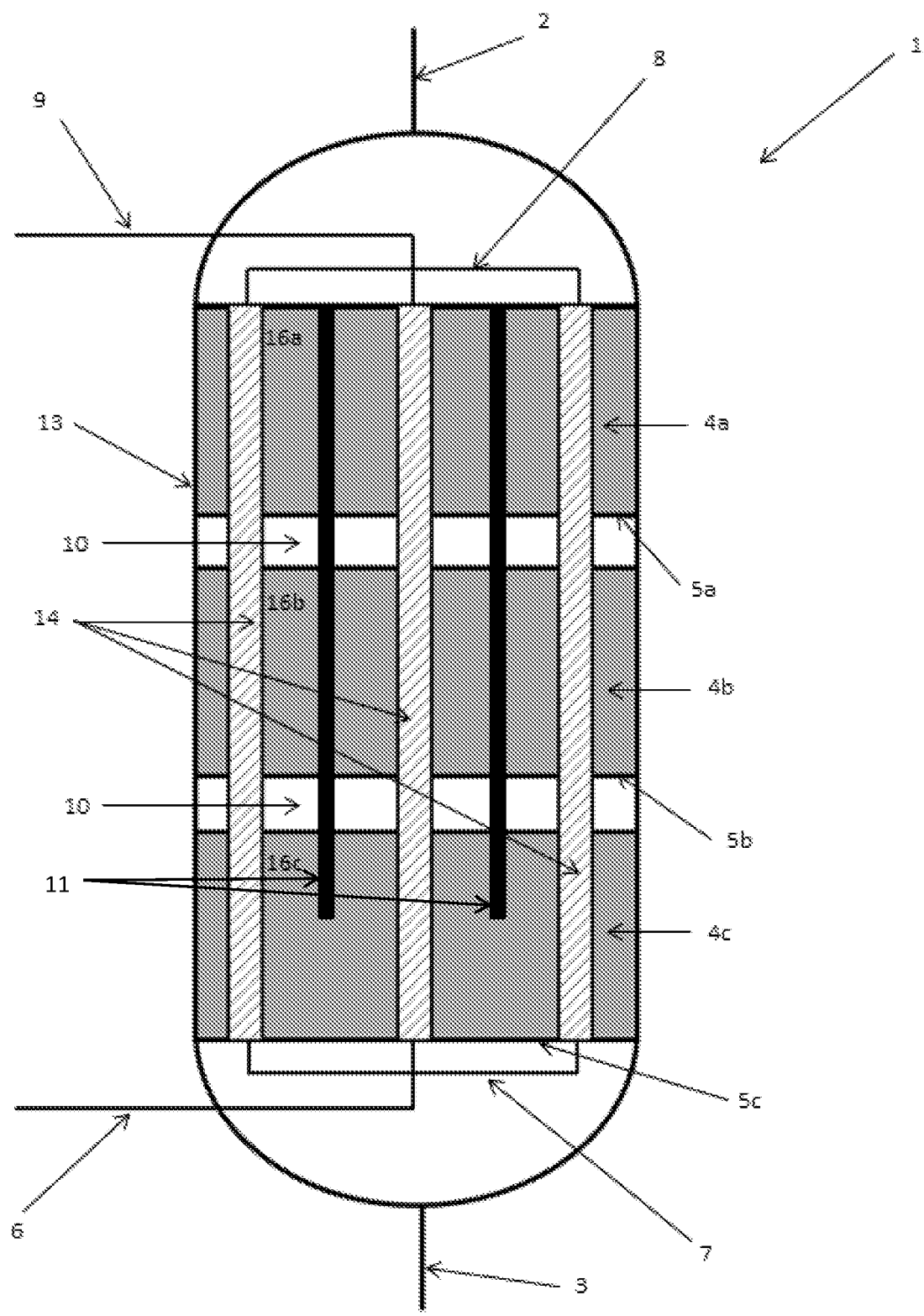
FIG. 2 is a schematic cutaway side view of a reactor according to another embodiment of the present disclosure.

The present disclosure is described in the following various non-limiting embodiments, which relate to an isothermal reactor and method for maintaining a substantially uniform temperature profile in the reactor in which a thermochemical reaction is taking place.

General Terms

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Each example of the present disclosure described herein is to be applied mutatis mutandis to each and every other example unless specifically stated otherwise. The present disclosure is not to be limited in scope by the specific examples described herein, which are intended for the purpose of exemplification only. Functionally-equivalent products, compositions and methods are clearly within the scope of the disclosure as described herein.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be clearly understood that, although a number of prior art publications are referred to herein, this reference does not constitute an admission that any of these documents forms part of the common general knowledge in the art, in Australia or in any other country.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. In case of conflict, the present specification, including definitions, will control.

In addition, the materials, methods, and examples are illustrative only and not intended to be limiting.

Specific Terms

The term 'isothermal reactor' as used herein refers to a vessel defining one or more chambers therein in which a reaction proceeds under substantially constant temperature conditions.

The term 'reaction zone' as used herein refers to any part of or all of a chamber or sub-chamber in a reactor where a reaction between the one or more reactants occurs. A reaction zone may be specifically defined in the reactor by various means including, but not limited to, depth in the reactor, volume in the reactor, particular temperature or pressure ranges, or by porous or permeable plates to delineate ingress and egress of the one or more reactants (and product) into and from the reaction zone.

The term 'space velocity' as used herein refers to the quotient of the entering volumetric flow rate of the reactants divided by the reactor volume (or the catalyst bed volume) which indicates how many reactor volumes of feed can be treated in a unit time.

The term 'tube pitch' as used herein refers to a geometrical tube layout arrangement in which as many tubes as possible are included within the reactor shell to achieve maximum heat transfer area. There may be four tube layout patterns including triangular (30°) or rotated triangular (60°) whereby the tubes are arranged with their centres at the apices of an equilateral triangle, and square (90°) or rotated square (45°) whereby the tubes are arranged with their centres at the corners of a square. Typically, the conventional arrangement of tubes is either on a regular equilateral triangle or on a square. A 'mid-point' in the tube layout arrangement refers to a point which is equidistantly spaced between either four adjacent tubes in a square tube layout arrangement or three adjacent tubes in a triangular tube layout arrangement.

The terms 'catalyst material' and 'solid catalyst' as used herein refers to a substance which actively facilitates a reaction between one or more reactants. Support materials such as aluminas, silicas, and other catalyst support materials, as are well known in the art are included within the definition of catalytic material as used herein. Promoters, activators, and other materials that facilitate catalyst are also included within the definition of catalytic material. The catalyst material may also include absorbent materials which do not promote a reaction, but rather adsorb a component, or components, of mixtures that they are exposed to. An adsorbent may also have catalytic properties, and a catalyst may act as an adsorbent Reactor for Thermochemical Reactions The present disclosure relates to a reactor for thermochemical reactions. The reactor may be any suitable reactor in which thermochemical reactions occur and typically comprises a reactor shell 13 having an inlet 2 for receiving one or more reactants and an outlet 3 for the removal of one or more products of the thermochemical reaction. The reactor is provided with at least one reaction zone 4a, 4b, 4c comprising a solid catalyst 16 in which at least a portion of the reactants undergo a thermochemical reaction. A heat exchange zone is provided, configured to exchange heat with the at least one said reaction zone as the thermochemical reaction progresses. The at least one reaction zone 4a, 4b, 4c or the heat exchange zone are housed in a plurality of tubes 14. To assist in the heating or cooling of the reaction zones and reduce the formation of hot or cold spots in the reaction zones, one or more inserts are provided, extending at least partially through one or more reaction zones.

The inserts comprise a central core spaced apart from the heat exchange zone by the solid catalyst 16. The positioning of the central core of the insert and the optional web members avoid hot or cold spots by regulating the quantity of reactants and catalyst material which partake in an endothermic or exothermic reactions as well as regulating the relative distribution of the reaction zone and the heat exchange zone, thereby regulating the net flow of heat.

Reactors according to the present disclosure will be discussed in more detail below in relation to tube reactors, i.e. tube cooled reactors and multi-tubular reactors. However, it will be appreciated that the inserts of the present disclosure can be provided to a variety of reactors for thermochemical reactors to maintain a desired temperature profile in the reactor.

Tube Cooled Reactor

In some embodiments, the present disclosure relates to a tube cooled reactor in which the plurality of tubes house the heat exchange zone.

Referring initially to FIGS. 1 to 4, where like features are referred to with like numbers, there is provided a reactor 1 for thermochemical reactions between one or more reactants. The reactor 1 comprises a reactor shell 13 having an inlet 2 for receiving one or more reactants and an outlet 3 for the removal of one or more products of the thermochemical reaction. In this particular embodiment, the reactor is provided with three reaction zones 4a, 4b, 4c in which at least a portion of the one or more reactants undergo a thermochemical reaction, and a plurality of parallel longitudinally extending heat exchangers 14.

The plurality of heat exchangers 14 extend longitudinally through the reaction zones 4a, 4b, 4c. The heat exchangers 14 may be any suitable device for transferring heat to or from the reaction zones 4a, 4b, 4c. In the present embodiment, the heat exchangers 14 are heat exchange tubes through which a heat exchange fluid, in this instance a cooling fluid, flows.

The cooling fluid may flow in a counter-current direction or a co-current direction to the flow of the reactants through the reactor 1. In the embodiments shown in FIGS. 1 to 4, the cooling fluid flows in through a heat exchange fluid inlet 6 before being distributed to the heat exchange tubes 14 via a heat exchange fluid distributor 7. The cooling fluid flows through the heat exchange tubes 14 in a counter-current direction to a flow of the reactants in the reactor 1, whereupon the cooling fluid is collected via a heat exchange fluid collector 8, and subsequently flows out of the reactor 1 via a heat exchange fluid outlet 9.

Referring to FIGS. 6 to 10, the heat exchange tubes 14 may be arranged in a square pitch. Alternatively, the heat exchange tubes 14 may be arranged in a triangular pitch. The number, length and outer diameter of the heat exchange tubes 14 in the reactor 1 determines the remaining space in the reactor 1 through which the one or more reactants flow.

A catalyst material 16 may be present in different amounts, concentrations, forms and configurations in each of the reaction zones 4a, 4b, 4c. The presence of any mechanical apparatus necessary to position the catalyst material 16 within the respective reaction zones 4a, 4b, 4c will be understood by one skilled in the art. Such mechanical apparatus may include, by way of illustrative example only, catalyst containers, holders, baskets, racks or nets. Similarly, any suitable configuration may be employed for catalytic material 16. For example, fixed bed, fluidised bed, slurry phase, among others may be used. Accordingly, the size and physical form of the catalyst material 16 may vary depending on the type of reaction and the reaction zone 4a, 4b, 4c in which they are to be used.

In this particular embodiment, the first reaction zone 4a comprises a bed of catalyst material 16a which comprises particles of active catalyst and optionally particles of an inert material with respect to the reaction occurring in the reactor 1. The catalyst material 16a is supported on a support plate 5a having a plurality of apertures therein to allow flow of reactants and products from first reaction zone 4a to second reaction zone 4b.

Second reaction zone 4b and third reaction zone 4c are similarly provided with a catalyst material 16b, 16c supported on a support plate 5b, 5c, respectively. Although the reaction zones 4a, 4b, 4c are depicted as having the same height, it will be appreciated that the reaction zones 4a, 4b, 4c may be varied in height and/or volume, as well as variations in the relative amount of the catalyst material (i.e. ratio of catalyst to inert material) depending on the requirements of the reactor 1.

One or more reaction-free zones 10 may also be provided between adjacent reaction zones 4a, 4b, 4c to assist in the heating or cooling of the reactant/product mixture exiting one reaction zone and prior to entering the subsequent reaction zone. The volume of the reaction-free zones 10 can be varied, for example by varying the height of the reaction-free zones 10, depending on the amount of heat transfer required for the reactor.

The reactor 1 further includes a plurality of longitudinally extending inserts 11 spaced apart from the heat exchangers 14 in parallel alignment therewith. The insert 11 may be positioned in a space defined between a plurality of adjacent heat exchange tubes 14 arranged in a particular tube layout arrangement.

Figure 6:
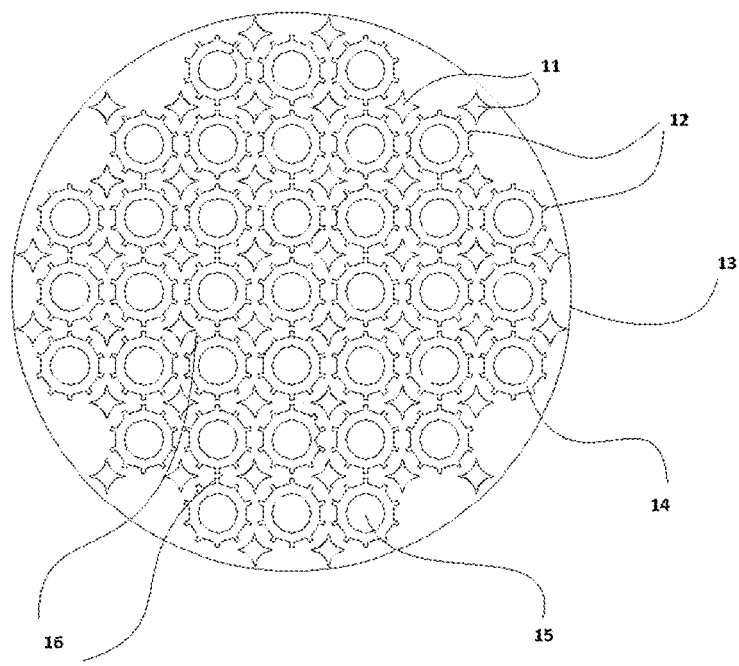
FIG. 6 is a cutaway top view of a reactor according to an embodiment of the present disclosure.

To reduce the radial temperature variation of the catalyst material 16 relative to the heat exchange tube 14, each insert 11 may be equidistantly spaced from the adjacent tubes 14. In a preferred embodiment each insert 11 is spaced apart from the heat exchangers 14 at the midpoint of four heat exchangers forming the square pitch as shown in FIG. 6. In this way, a more uniform temperature profile within any reaction zone 4 in the reactor 1 can be provided by reducing the maximum distance of the catalyst material from the nearest cooling tube 14.

In the embodiments described with reference to the Figures, the core of each insert 11 is coincident with a mid-point between four adjacent heat exchangers 14 arranged in a square pitch. It will be appreciated by those skilled in the art that in alternative embodiments wherein the heat exchangers 14 are arranged in a triangular pitch, each insert 11 may be coincident with a mid-point between three adjacent heat exchangers 14.

The effect of the inserts 11 is to reduce the available space which can be occupied by the catalyst material 16a, 16b, 16c in the reactor 1. Consequently, the volume of catalyst material used in the reactor may be reduced, which in turn may reduce the amount of heat generated by the exothermic reaction.

It will be appreciated that the shape and cross-sectional area of the inserts 11 may be varied to achieve the desired volume of the catalyst material 16 in a reaction zone 4a, 4b, 4c by displacing the appropriate volume of catalyst material 16 from voids between adjacent heat exchangers 14.

As described in more detail below with reference to FIG. 6, in addition to reducing the effective volume of catalyst material 16a, 16b, 16c in the reactor 1, the inserts 11 may be positioned at respective midpoints between adjacent heat exchangers 14 to reduce the maximum distance between the catalyst material 16a, 16b, 16c and the heat exchangers 14, thus providing a more uniform temperature profile across the reactor 1.

In the embodiment shown in FIG. 1, the inserts 11 may have a constant diameter along their length and extend through each of the reaction zones 4a, 4b, 4c.

However, the thermal energy released or absorbed by the thermochemical reaction is typically higher proximal to the inlet 2 than the thermal energy released or absorbed proximal to the outlet 3 because the concentration of reactants available to undergo reaction is greater proximal to the inlet 2. Consequently, it may not always be necessary to extend the inserts 11 through each of the reaction zones 4a, 4b, 4c. In an alternative embodiment shown in FIG. 2, the inserts 11 only partially extend through the third reaction zone 4c. In this embodiment, the inserts 11 extend through the reaction zones 4a, 4b closest to the inlet 2 and only partially extend through the reaction zone 4c closest to the outlet 3. As will be appreciated, some inserts may extend through each of the reactions zones and other inserts may partially extend through the reaction zones.

Figure 3:
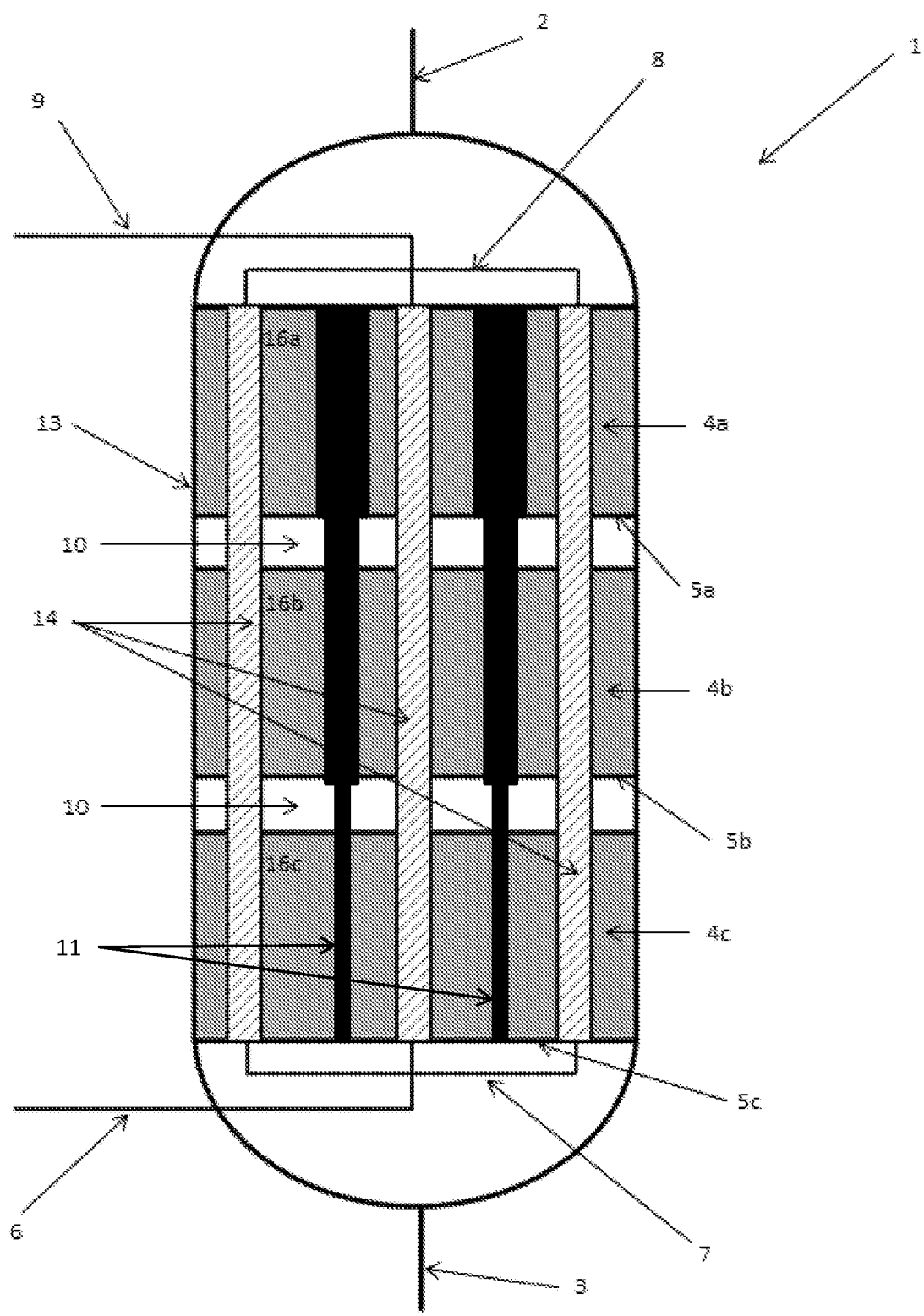
FIG. 3 is a schematic cutaway side view of a reactor according to an alternative embodiment of the present disclosure.
Figure 4:
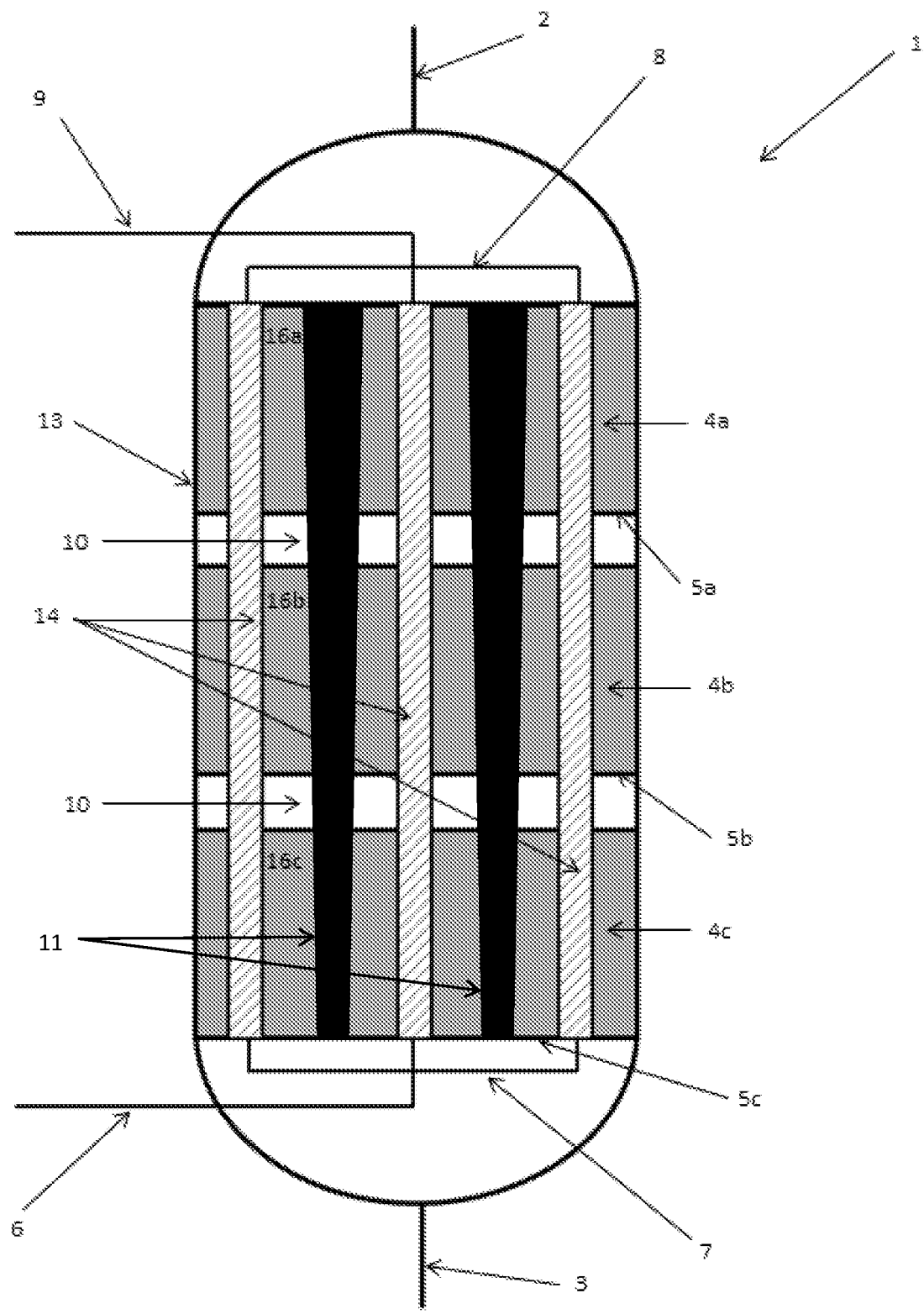
FIG. 4 is a schematic cutaway side view of a reactor according to a further alternative embodiment of the present disclosure.

As discussed above, the thermal energy released or absorbed by the reaction is typically greater in the first reaction zone 4a closest to the inlet 2 and lower in the third reaction zone 4c closest to the outlet 3. To provide a more uniform temperature profile in the reactor 1 from the inlet 2 to the outlet 3, a cross-sectional area (e.g. diameter) of the insert 11 may vary along its length as shown in FIGS. 3 and 4. In these particular embodiments, the diameter of the inserts 11 decreases along the length of the inserts 11 from an end thereof proximal the inlet 2 to an end thereof distal the inlet 2. In this way, the maximum distance between the catalyst material 16a, 16b, 16c and the heat exchangers 14, as well as the volume of the catalyst material is less in reaction zone 4a closest to the inlet 2 than the volume of catalyst material in a reaction zone 4c closest the outlet 4.

The cross-sectional area or diameter of the inserts 11 may vary in a discrete, stepped manner as shown in FIG. 3, or may vary in a continuous manner as shown in FIG. 4. Advantageously, reducing the catalyst volume by varying the cross-sectional area or diameter of the inserts 11 in this way may also avoid the current practice of providing varying dilutions of the catalyst with inert materials to alter the volume of catalyst in a particular reaction zone.

Figure 5:
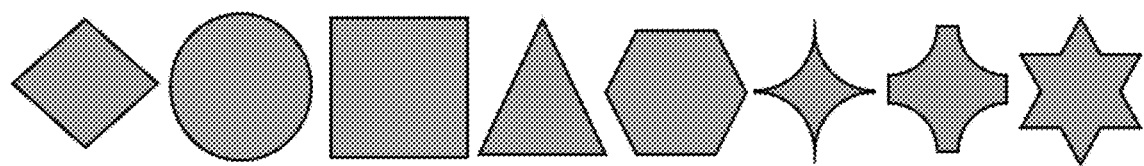
FIG. 5 is a cross-sectional view of a number of embodiments of inserts according to the present disclosure.

FIG. 5 shows several possible cross-sectional shapes for the inserts 11. Suitable cross-sectional shapes include, but are not limited to, diamond, circular, square, triangular, hexagonal, star-shaped, and shapes with 4-sided symmetry having curved concave lines. The shape and cross-sectional area of the inserts 11 can also be varied along the length of the reactor 1 to provide an optimal ratio of heat transfer area to volume of catalyst at each point in the reactor. It will be appreciated that various combinations of the above described inserts 11 can be used depending on the requirements of the reactor 1. The cross-sectional shape of the inserts 11 may also be selected to improve the flow of reactants and products through the reactor 1.

The cross-sectional shape of the inserts 11 may be selected to correspond to the general curvature of the tubes 14. In the embodiment shown in FIG. 6 for example, diamond shaped inserts 11 with concave curved edges are positioned equidistantly between adjacent tubes 14. The curved surfaces of the inserts 11 correspond to the general curvature of the tubes 14 to provide a substantially annular void around each tube 14 which reduces the temperature variation across the reactor. In use, the annular void between the solid inserts 11 and the tubes 14 is occupied by the catalyst material 16.

In the embodiment shown in FIG. 6, the heat exchange tubes 14 are configured with a plurality of fins 12 extending along the length of the heat exchange tubes 14 for enhancing the heat transfer area between the catalyst 16 and tubes 14. The fins 12 enhance the heat transfer area, while the inserts 11 placed between the tubes 14 reduces the radial distance of the catalyst material from the surface of adjacent tubes 14. Depending upon the expected heat generation/absorption rates of different exothermic or endothermic reactions, the size of the fins 12 and volume of the inserts 11 can be altered to maintain a desired specific heat transfer area.

Figure 7:
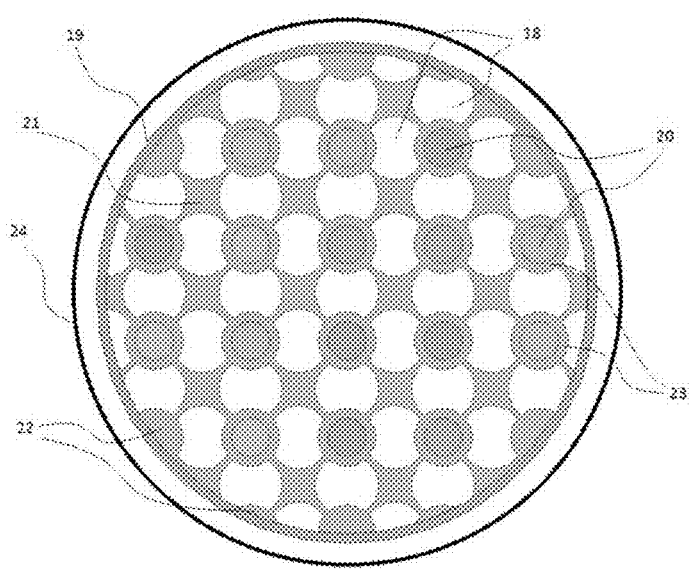
FIG. 7 is a cutaway top view of a reactor according to an embodiment of the present disclosure.

In another embodiment shown in FIG. 7, heat exchange tubes 23 are placed in a square pitch with the inserts 21 placed at the mid-point between four adjacent tubes 14. The tubes 14 have radially extending fins 12 integrally connected along the length of the insert 23. The catalyst material occupies the cavities 18 defined between the inserts 21 and the tubes 23. The reactants flow through the catalyst material held in the cavities 18 and react in the presence of catalyst to form product and release or absorb heat. Inside the tubes 23, a heat exchange fluid flows through a flow conduit 20. The heat exchange fluid transfers heat to or from the catalyst material 18 in order to maintain a steady state temperature profile inside the reactor.

In a typical tube-cooled reactor, hot spots can occur at the wall surfaces of the reactor as an increased volume of catalyst is present at the wall surface in comparison to within the body of the reactor. This is due to the increased radial distance between the outer cooling tubes and the wall as compared to the distance between adjacent inner cooling tubes. Furthermore, the wall surface of the reactor is often not cooled. To mitigate the formation of hotspots at the wall surfaces, in the embodiment shown in FIG. 7, additional inserts 22 are also provided on the inner wall of the reactor shell 19. As depicted in FIG. 7, the entire reactor shell 19 may also be covered with a metal jacket 24 through which additional heat transfer fluid flows to transfer heat to and from the catalyst material held in the cavities 18 and the additional inserts 22, 23 connected to the reactor shell 19.

It will be appreciated that the inserts 11, 22 of the present disclosure can be retro-fitted to existing catalytic reactors. The type, number, position, cross-sectional shape, diameter, length and material can be selected based on the characteristics of the reactor to which the inserts are to be introduced.

Figure 8:
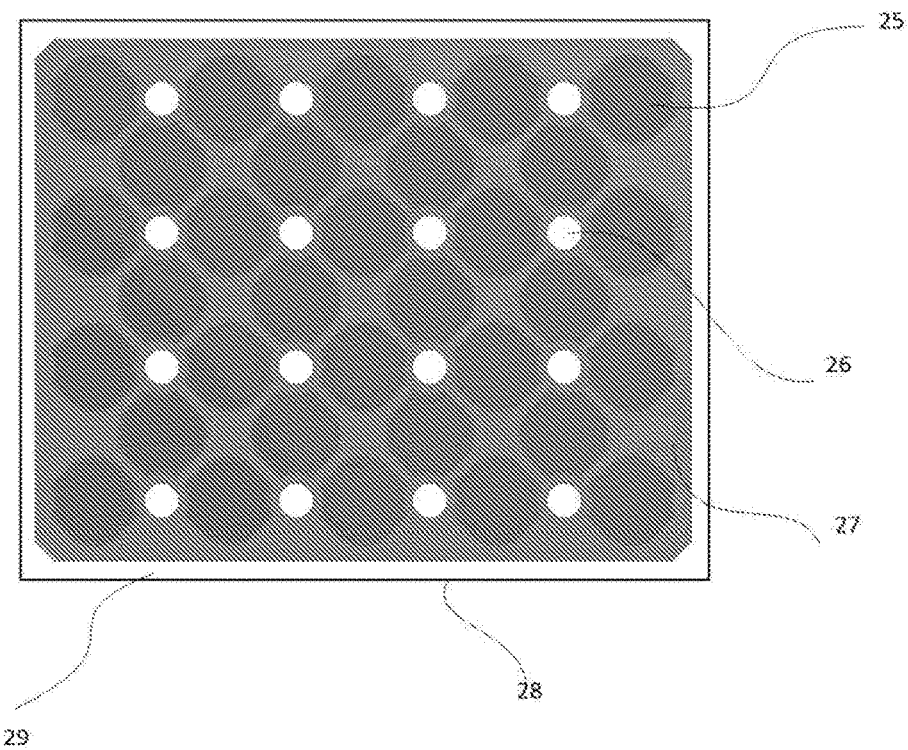
FIG. 8 is a cutaway top view of a reactor according to an embodiment of the present disclosure.

In the embodiment shown in FIG. 8, the heat exchange tubes 26 and inserts 11 may be cast in a single block 27. The block 27 may then be positioned inside a shell 28 in an arrangement whereby heat exchange fluid flows through an annulus 29 surrounding the block 27. The volume provided by the catalyst cavities 25 and the heat transfer area provided by the cooling tubes can be predetermined according to well known techniques so that the required specific heat transfer area is maintained throughout the reactor.

Figure 12:
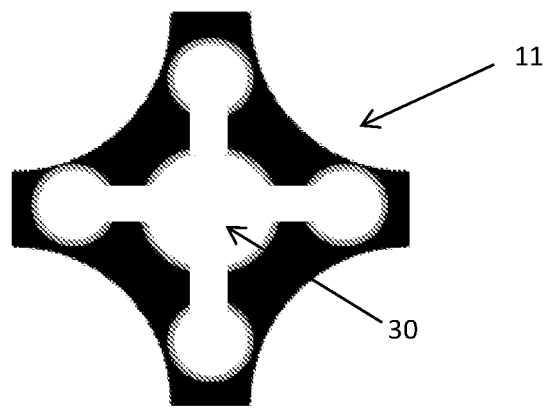
FIG. 12 is a cross-sectional view of an insert according to the embodiment shown in FIG. 11.
Figure 11:
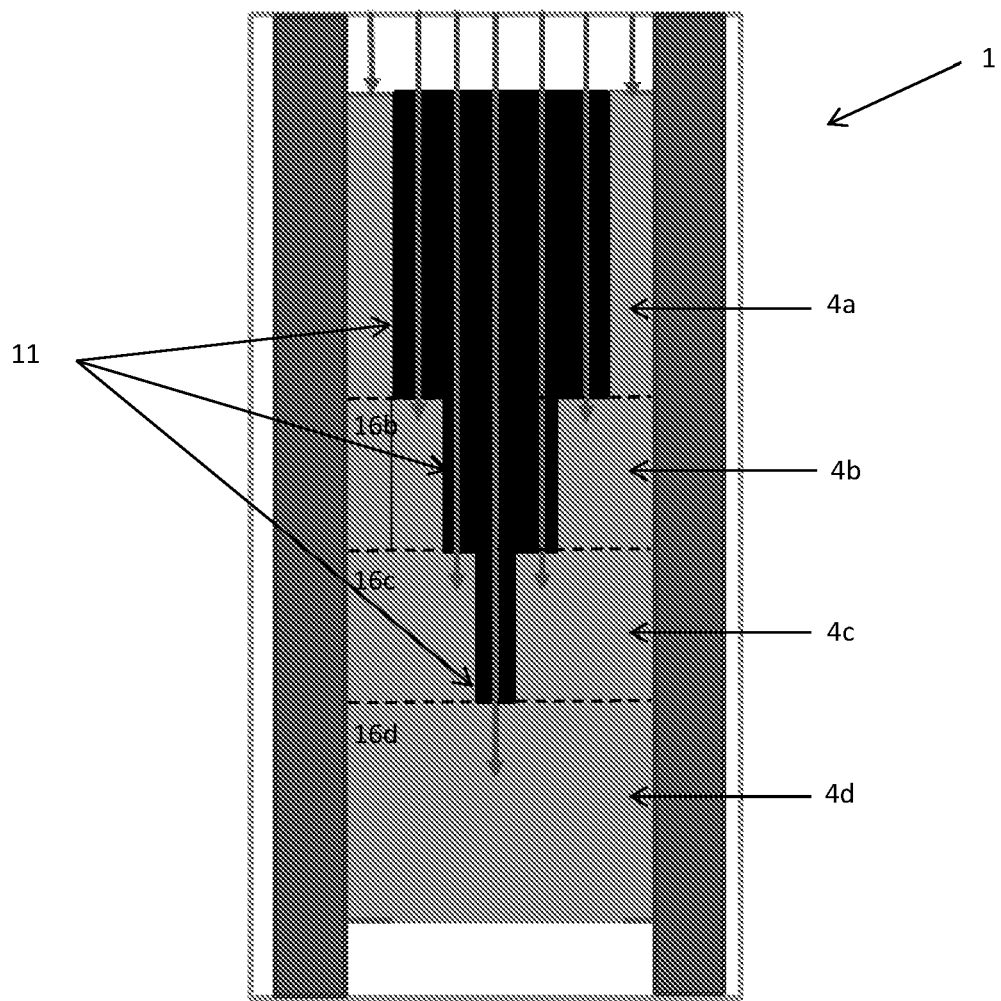
FIG. 11 is a schematic cutaway side view of a reactor according to an alternative embodiment.

As discussed in more detail below, bypassing can also be utilised to reduce the variation in temperatures along the reactor and/or optimise reactor performance. For example, in some embodiments of the tube cooled reactor, the insert 11 may be configured to provide a flowpath for one or more reactants to bypass one or more reaction zones in the reactor 1. Referring to FIGS. 11 and 12, the insert 11 may be provided with a longitudinally extending bore 30 extending through the entire length of the insert 11. A plurality of inserts 11 of differing lengths may be provided, such that the flow of unreacted reactants from the inlet flows along the length of the insert 11 directly to a selected reaction zone 4a, 4b, 4c, 4d in the reactor 1.

In alternative embodiments shown in FIGS. 13a, 13b, 14a and 14b, in addition to being provided with a longitudinally extending bore 30, the insert 11 may also be provided with one or more laterally extending bores 31, 32 in fluid communication with the longitudinally extending bore 30 and a selected reaction zone. In this way, the reactants can egress (FIG. 14a) and ingress (FIG. 14b) the insert 11 via the laterally extending bore 31, 32 such that the flow of at least a portion of the reactants can bypass one or more reaction zones 4a, 4b, 4c, 4d.

In some embodiments, as shown in FIG. 13a, the insert 11 may comprise an assembly of insert portions 11a which, when assembled, define a longitudinally extending passage 30' with one or more laterally extending passages 31', 32'. The assembly of insert portions 11a may be supported by the catalyst material in the reactor 1. Alternatively, the assembly of insert portions 11a may be supported in the reactor 1 in a frame or are cast within the block 27 as described above, or may be supported by support plates 5a, 5b, 5c.

The inserts 11 may be formed of any suitable non-reactive material. In a preferred embodiment, the inserts 11 are formed of a thermally conductive material, such as a metal, that allows the transfer of heat from reaction zones 4a of higher temperature to reaction zones 4c of lower temperature, thus also contributing to minimising variations in temperature across the reactor 1.

Multi-Tubular Reactor

In some embodiments, the present disclosure relates to a multi-tubular reactor in which the plurality of tubes house the at least one reaction zone.

Multi-tubular reactors are similar to tube cooled reactors, however in multi-tubular reactors the catalyst is provided in a plurality of reaction tubes running longitudinally through the reactor shell, and the cooling medium flows through the reactor shell in contact with the outer surface of the reaction tubes.

A multi-tubular reactor for thermochemical reactions according to an embodiment of the present disclosure comprises a reactor shell having an inlet for receiving reactants into the reactor and an outlet for the removal of products from the reactor. A plurality of reaction tubes 14', as shown for example in FIG. 16, extend longitudinally in the reactor shell.

Each reaction tube 14' defines at least one reaction zone in which at least a portion of the reactants undergo a thermochemical reaction. The reactor shell is configured to receive a heat exchange medium for exchanging heat with the reaction tubes 14'. For example, the reactor shell may be configured such that the heat exchange medium flows through an inlet at one end of the reactor, and out an outlet at another end of the reactor. The heat exchange medium may flow counter-currently or co-currently with the flow of reactants through the reactor.

A catalyst material may be provided in the reaction tube for promoting the thermochemical reaction of the reactants. As for the tube cooled reactor, the catalyst material may be present in different amounts, concentrations, forms and configurations along the length of the tube. One or more reaction-free zones may also be provided within the reaction tube' between adjacent reaction zones. The catalyst material may also optionally comprise particles of inert material with respect to the reaction occurring in the reactor.

The reaction tubes 14' further comprise inserts 11 extending longitudinally in the reaction tube 14'. The inserts 11 displace the catalyst from the centre of the reaction tube, thus reducing the maximum distance of the catalyst from the heating or cooling effects of the heat exchange medium. With reference to the insert shown in FIG. 16, the catalyst is positioned in the cavities defined between the outer surface of the insert 11 and the inner surface of reaction tube 14'. The insert 11 may be any suitable shape or material. Although shown in contact with the inner surface of the reaction tube 14', the insert 11 may also be spaced apart from the inner surface of the reaction tube 14'. For example, the insert 11 may be a solid cylindrical insert extending co-axially with the reaction tube 14'. Any additional features described above with reference to inserts for the tube cooled reactor may also be suitable for inserts used in the multi-tubular reactor.

Figure 16:
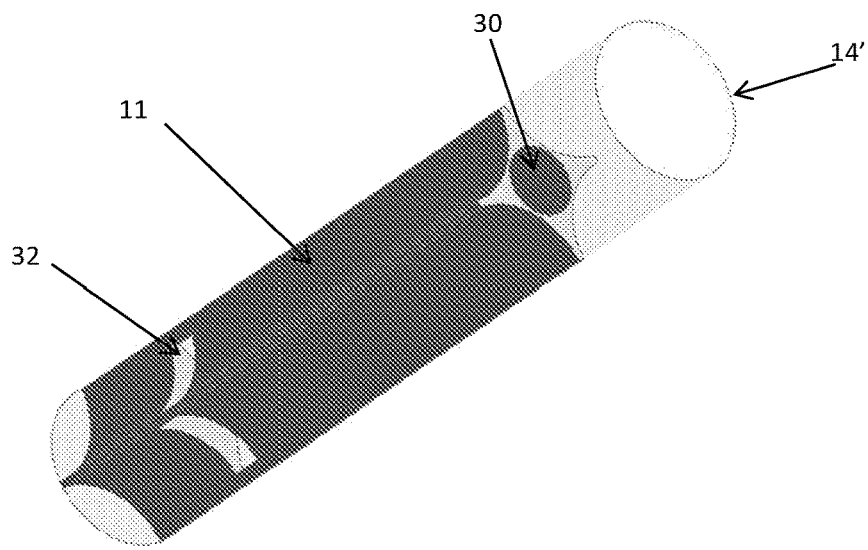
FIG. 16 is a perspective view of a reaction tube for use in a multi-tubular reactor according to yet another alternative embodiment of the present disclosure.

In some embodiments, the insert 11 may be configured to provide a flowpath for one or more reactants to bypass one or more reaction zones in the reactor tubes 14'. The insert 11 may extend part of the length of the reaction tube 14' and be provided with a longitudinally extending bore 30 extending through the entire length of the insert. In alternative embodiments, such as is shown in FIG. 16, in addition to being provided with a longitudinally extending bore, the insert 11 may also be provided with one or more laterally extending bores 32 in fluid communication with the longitudinally extending bore 30 and a selected reaction zone. In this way, the reactants can egress and ingress the insert 11 via the laterally extending bore 32 such that the flow of at least a portion of the reactants can bypass one or more reaction zones.

In some embodiments, the insert 11 may comprise an assembly of insert portions, for example as described in relation to FIG. 13a above.

Calculation of Area of an Insert

Although the inserts of the present disclosure have been discussed with respect to use in a tube reactor, it will be appreciated that the inserts of the present disclosure can also be used in a number of reactors for controlling the temperature profile therein. An example of the calculations for determining the size and number of inserts for a system are provided below.

Figure 9:
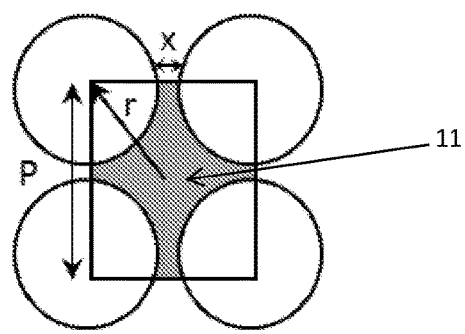
FIG. 9 is a diagrammatic representation of an insert according to an embodiment of the present disclosure.

Referring to FIG. 9, the area of the insert 11 is calculated using the following formula:

Area of insert=$P^2-\pi r^2$

If $x=0$:

Area of insert=$r^2(4-\pi)$

Generic Formulas for Calculating the Number of Inserts, Tubes and Shell Diameters Heat Exchange Tubes The parameters of heat exchange tubes are as follows:
Outside diameter=$D_t$
Inside diameter=$D'_t$
Number of tubes=$N_t$
Length of tube=$L_t$
Pitch=$Z_t$
Pitch type=Triangle/Square/Rotated Triangle/Rotated Square Calculating Areas of Inserts of Different Shapes For a star shape:

$$\text{Area}(A_i) = P_{st}^2 - \frac{\pi}{4} 2r^2$$

where:
Radius=r
Thickness=X
Pitch (Insert)=$P_{st}$
Length=$L_{st}$
For a square/rectangle shape:

$$\text{Area}(A_i) = P_{sq} * L_{sq}$$

where:
Width=$P_{sq}$
Length=$L_{sq}$
For a triangle shape:

$$\text{Area}(A_i) = P'_t * P''_t P'''_t$$

where:
Side 1=$P'''_t$
Side 2=$P''_t$
Side 3=$P'''_t$
For a circle shape:

$$\text{Area}(A_i) = \frac{\pi}{4} 2r_{cir}^2$$

where: Radius=$r_{cir}$

It will be appreciated that the area of an insert can be similarly determined for any shape and is not limited to the above examples.

Deriving a Generic Formula for Specific Heat Transfer

A method for deriving a generic formula for specific heat transfer is demonstrated below, where:
Specific heat transfer=$S_{ht}$
Area of pitch=$A_p$
Area of insert=$A_i$
Axial length of insert=$L_i$
Shell diameter (reactor)=$D_s$
Number of inserts=$N_i$ For a given shell diameter, there can be a maximum number of tubes in one direction depending on the tube layout (generally defined by the Principles of the Tubular Exchanger Manufacturers Association (TEMA) code for heat exchangers).

For reactors according to the present disclosure, the maximum number of tubes in one direction can be calculated as follows:

$$N_D^{max} = \text{int}\left(\frac{D_s}{Z_t}\right)$$

For each repetitive cell (defined as an insert surrounded by at least more than one heat exchange tube), a free area of the reactor ($A_f$) that can be filled with the catalyst material can be calculated as:

$$A_f = A_p - A_i - \sum_{n=1}^{n} A_t$$

where, $$A_t = \frac{\pi}{4} D_t^2 * \alpha_t$$

and $\alpha_t$ is defined as the fraction of the heat exchange tube exposed to the cell. For example, in a square pitch $\alpha_t=0.25$, and in a triangle pitch $\alpha_t=0.33$.

The total free area of a reactor which can be filled with the catalyst material ($A_f^t$) can be calculated as:

$$A_f^t = \sum_{n=1}^{n} A_f$$

Assuming the shape of the insert does not change in the axial direction, the volume of the catalyst material that can be loaded ($V_c$) can be calculated as:

$$V_c = A_f^t * L_i$$

If $\rho_c$ is the bulk density of the catalyst material, then the maximum weight of the catalyst ($W_c$) that can be loaded is calculated using:

$$W_c = V_c * \rho_c$$

Figure 10:
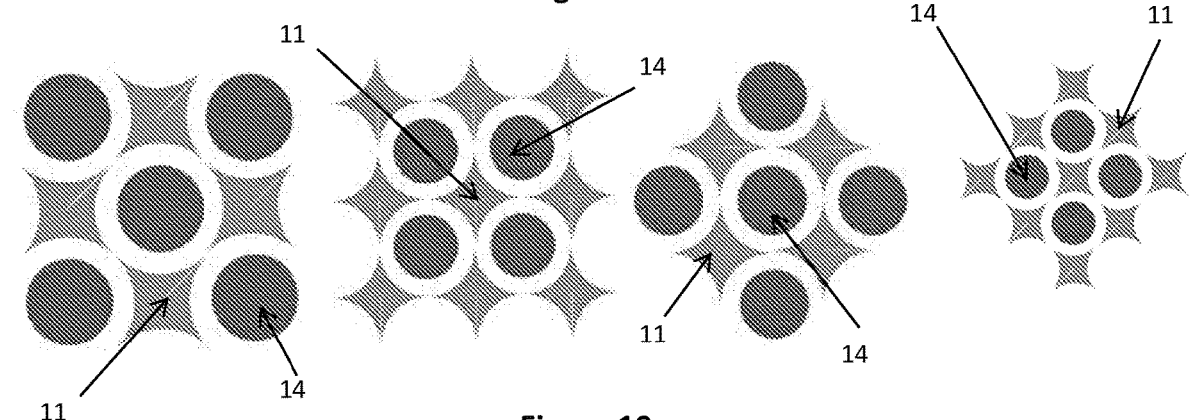
FIG. 10 is a schematic view of various pitch arrangements of inserts and heat exchangers according to embodiments of the present disclosure.

It should be noted that in order to calculate the total heat transfer area, the tube layout must be considered in order to determine how many sides of the heat exchange tube are exposed to the catalyst material and also taking into account boundary effects near the reactor shell wall. The four potential pitch types that can govern the layout are demonstrated in FIG. 10. The maximum number of cells (as shown in FIG. 10) is defined as $c_{max}$.

For each cell, the heat transfer area ($H_t^i$) can be written as:

$$H_t^i = \sum_{j=1}^{j} (\pi * D_t * L_t) * \alpha_t$$

where:
j=4 for square and rotated square pitch
j=3 for triangle and rotated triangle pitch The total heat transfer area ($H_t$) can be calculated as:

$$H_t = \sum_{c=1}^{c=c_{max}} H_t^i$$

Finally, the specific heat transfer area ($S_{ht}$) can be calculated as:

$$S_{ht} = \frac{\sum_{c=1}^{c=c_{max}} H_t^i}{V_c} \approx \frac{\sum_{c=1}^{c=c_{max}} H_t^i}{W_c}$$

where the units of $S_{ht}$ can be $m^{-1}$ or $m^2\ kg^{-1}$.

Bypassing Reaction Zones

The present disclosure further relates to reactors for thermochemical reactions comprising hollow inserts that function as flow diverters.

The use of flow diverters may also assist in minimising temperature variations in the reactor by directing the flow of reactants and/or a heat exchange medium through the reactor. The flow diverters may also be used to control and balance space velocity within the reactor to enhance reactor performance. In such a reactor, there is provided a reactor shell having an inlet for receiving reactants into the reactor and an outlet for the removal of products from the reactor. The reactor comprises two or more reaction zones in which at least a portion of the reactants undergo a thermochemical reaction. In some embodiments, such as is shown in FIGS. 11, 14a, and 14b, a plurality of flow diverters are provided for directing portions of the reactants to selected reaction zones, wherein at least one portion of the reactants is directed to a different reaction zone to at least one other portion of the reactants. It will be appreciated that the hollow inserts may be provided in addition to or alternatively to the inserts described above.

In another embodiment, one or more inserts of the above described embodiments may be configured to also perform the function of a flow diverter, with the hollow inserts comprising an inlet and an outlet which is preferably sealable. In another embodiment, the inlet and outlet aperture size may be adjustable to enable the flow diverter adjusted to fine tune reactor performance. The ability to fine tune the proportion of a stream which is diverted is beneficial as the translation of reactor design to reality is still prone to variations in catalyst activity or distribution, in additional to reactant and reaction mixture concentration and space velocity variations, which cannot be accurately anticipated in the modelling of the reactor. Hence, the ability to adjust flowrate within the flow diverters and/or increase or decrease the number of flow diverters provide increased flexibility to maintain high reactor performance. In one embodiment, a portion or all of the inserts are capable of being converted to flow diverters.

The function of the inserts may be conveniently adjusted during the commissioning phase of the reactor and during maintenance shut-down periods, if required Changes in catalysts activity over time, may also require adjustments to the insert configuration and function.

As discussed above, for an exothermic reaction, the generation of heat in a standard reactor is typically greatest towards the inlet where there is the greatest concentration of reactants available for reacting with the catalyst. The heat generated by the reaction reduces along the reactor towards the outlet as more and more reactants react to form the products, reducing the available concentration of reactants. Within this embodiment, the proportion of the reactants which are diverted by the flow diverters from the reactant feed or within or immediately after the first reaction zone is preferably at least 20% more preferably at least 40% and even more preferably at least 60% by volume of the reactant feed stream or outlet of the first reaction zone. Similarly, the volume of inserts within the reaction zone is preferably at least 20% more preferably at least 40% and even more preferably at least 60% of the total reaction zone space (catalyst material, inserts and void space for reactant/reaction mixture flow).

According to certain embodiments of the present disclosure, this variation in heat generation along the length of the reactor can be reduced by directing the flow of the reactants to different sections of the reactor with the flow diverters.

In another embodiment, a reactor may be provided in which the temperature variations along the reactor are reduced by using flow diverters to direct flow of portions of a heat exchange medium to exchange heat with selected reaction zones, wherein at least one portion of the heat exchange medium is directed to exchange heat with a different reaction zone to at least one other portion of the heat exchange medium.

Methods for Reducing Temperature Variations in an Isothermal Reactor

The present disclosure also relates to methods for reducing temperature variations in an isothermal reactor.

Reactants are received into the reactor through the inlet 1 into a first reaction zone 4a. Upon contact with the catalyst material 16a, 16b, 16c a portion of the one or more reactants undergo a thermochemical reaction. Depending on the reactants and catalyst used, the reaction may be exothermic in which heat is released during the course of the reaction. Alternatively, the reaction may be endothermic in which heat is absorbed during the course of the reaction. The reactor 1 will generally be further described with respect to an exothermic reaction, however it will be appreciated that the reactor 1 can also be used for endothermic reactions where the heat exchangers 14 heat, rather than cool, the reaction zones 4a, 4b, 4c.

For the presently described exothermic reaction, as the reactants flow through the reaction zones 4a, 4b, 4c, a portion of the reactants react in the presence of the catalyst material 16a, 16b, 16c to produce the product and release heat. The heat released by the exothermic reaction is dissipated from the reaction zone 4a, 4b, 4c via the cooling tubes 14 which extend through the reaction zones 4a, 4b, 4c.

In a typical tube cooled reactor, the temperature of the catalyst material may vary radially from the surface of the heat exchange tubes. For example, for an exothermic reaction, the temperature of the catalyst material will be lowest at the surface of the cooling tubes, increasing in temperature with radial distance from the surface of the cooling tube. Adjacent cooling tube may be arranged in the tube cooled reactor in a square or a triangular pitch whereby the temperature of the catalyst reaches a maximum value at a mid-point between adjacent cooling tubes (i.e. the further distance from the surface of the adjacent cooling tubes) before decreasing to its minimum temperature at the surface of the adjacent cooling tube.

In the embodiments disclosed herein, a plurality of inserts 11 are disposed in spaced parallel arrangement with the cooling tubes 14. The effect of the inserts 11 is to reduce the available space which can be occupied by the catalyst material 16a, 16b, 16c in the reactor 1. Consequently, the volume of catalyst material used in the reactor may be reduced, which in turn may reduce the amount of heat generated by the exothermic reaction.

Furthermore, the inserts 11 are disposed at the mid-point between adjacent cooling tubes arranged in a square or triangular pitch. The insert 11 effectively displaces catalyst from the mid-point, shortening the maximum distance the catalyst can reside from the outer surface of the cooling tube. The temperature gradient of the catalyst material residing between the outer surface of the cooling tube and at its furthest point from the outer surface of the cooling tube is thereby reduced.

Alternatively or additionally, the reactor for thermochemical reactions may be operated to reduce temperature variations in the reactor by diverting portions of the reactants to selected reaction zones, wherein at least one portion of the reactants is directed to a different reaction zone to at least one other portion of the reactants.

Figure 15:
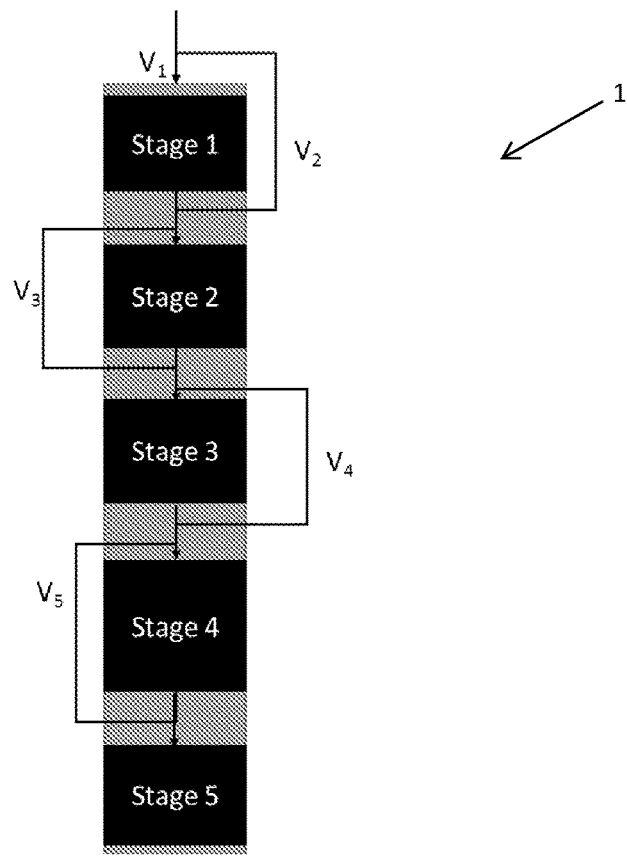
FIG. 15 is a schematic view of a reactor according to a further alternative embodiment of the present disclosure.

In one embodiment shown in FIG. 15, reactants entering the reactor first split into two flows V1, V2, where V1 is passed through a first reaction zone and V2 bypasses the first reaction zone via a flow diverter. V2 then mixes with the products of first reaction zone, a portion of which is fed to the second reaction zone and the remainder of which bypasses the second reaction zone via a flow diverter. This pattern may continue along the length of the reactor where, in the final reaction zone, all of the reactant/product gas stream is fed to the reaction zone. The ratio of the gas stream entering and bypassing any one reaction zone can be varied depending on the requirements of the reactor.

Further embodiments depicting the diversion of reactants are shown in FIGS. 11, 14a and 14b, and discussed in more detail above.

Alternatively or additionally, the reactor for thermochemical reactions may be operated to reduce temperature variations in the reactor by diverting portions of a heat exchange medium to exchange heat with selected reaction zones, wherein at least one portion of the heat exchange medium is directed to exchange heat with a different reaction zone to at least one other portion of the heat exchange medium.

Optimisation of Reactor Performance

Modelling was conducted to assess the effect of splitting the inlet/outlet streams of a number of reaction zones (as depicted in FIG. 15) and catalyst area on the temperature and yield of a tube reactor. The model was based on a Lurgi tubular reactor producing methanol.

Figure 17A:
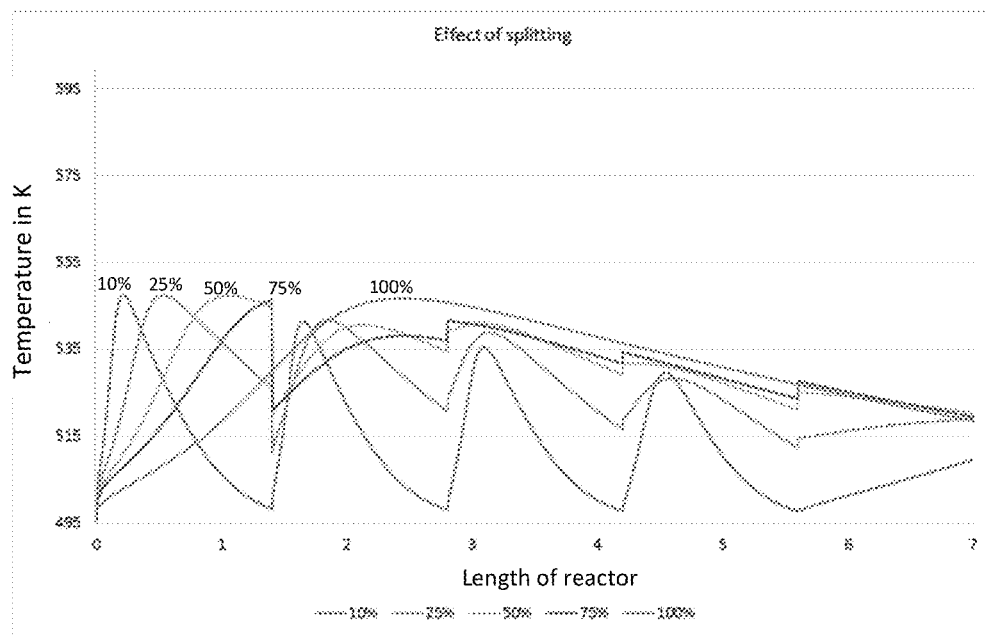
FIG. 17(a) is a graph demonstrating the effect of split ratio on temperature profile.
Figure 17B:
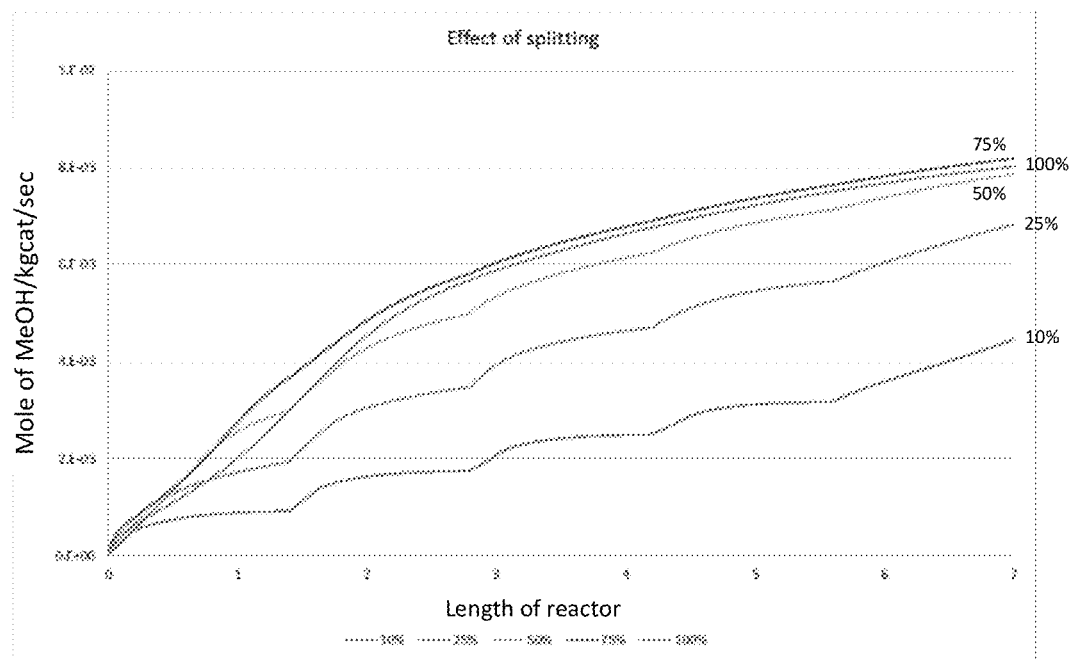
FIG. 17(b) is a graph demonstrating the effect of split ratio on methanol flow rate.

FIGS. 17(a) and 17(b) demonstrate the effect of the percentage of an inlet stream to a given stage on the temperature and methanol concentration along the length of a reactor. The results are shown for an equal percentage split in every stage of the reactor. Referring to FIG. 15, for a 100% split, 100% of the flow from each stage flows into the subsequent stage. For a 10% split, 10% of the combined flow from the outlet and bypass of the previous stage flows to the subsequent stage.

Figure 18A:
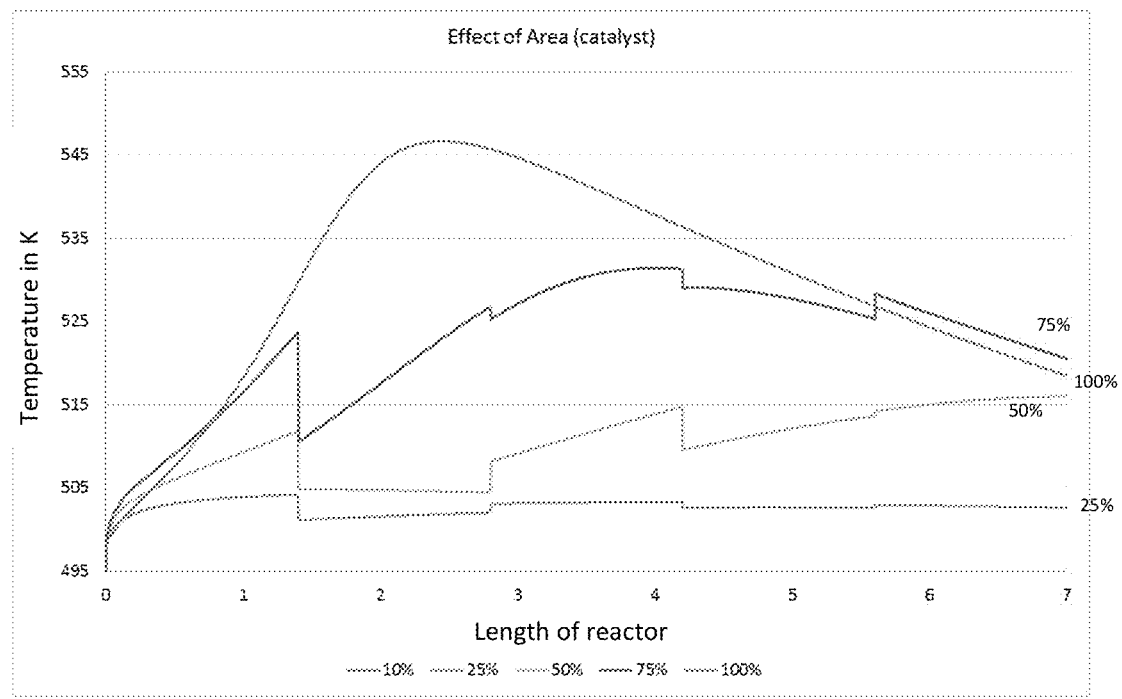
FIG. 18(a) is a graph demonstrating the effect of catalyst area on temperature profile.
Figure 18B:
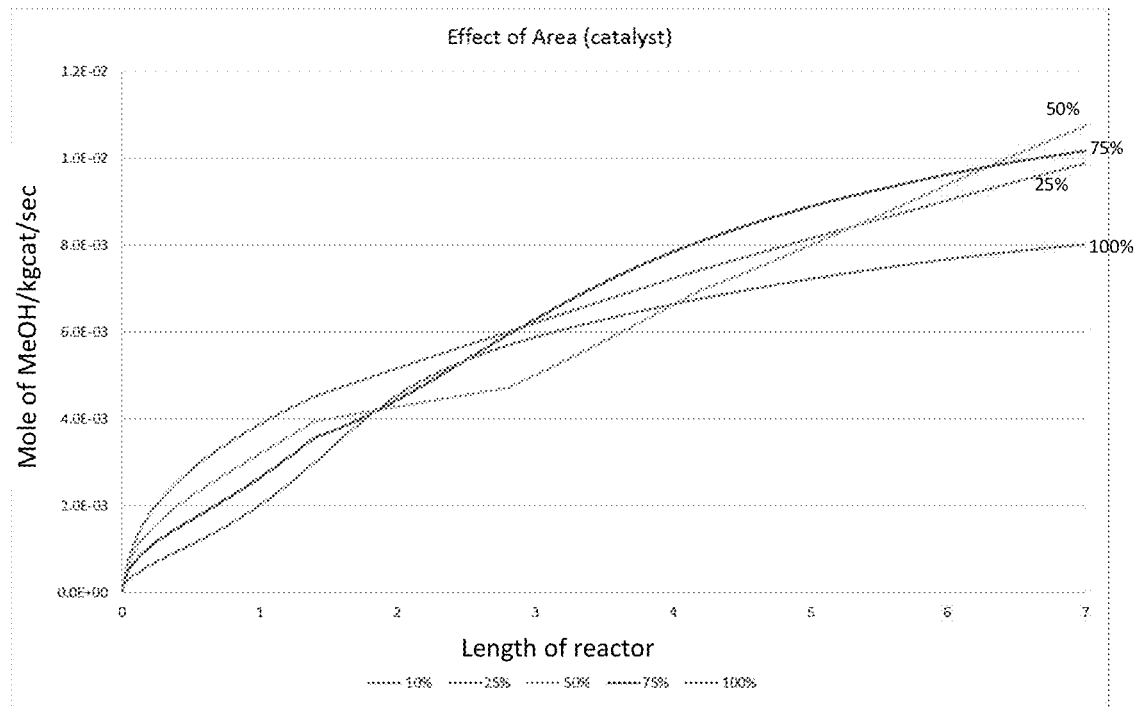
FIG. 18(b) is a graph demonstrating the effect of catalyst area on methanol flow rate.

FIGS. 18(a) and 18(b) demonstrate the effect of catalyst area (i.e. assuming that a portion of the area had not reacted due to, for example, the presence of inserts) on the temperature and methanol concentration along the length of a reactor. As can be seen in FIG. 18(b), the productivity of the reactor was improved when the area of the catalyst was reduced by 25%, 50% and 75%.

Figure 19A:
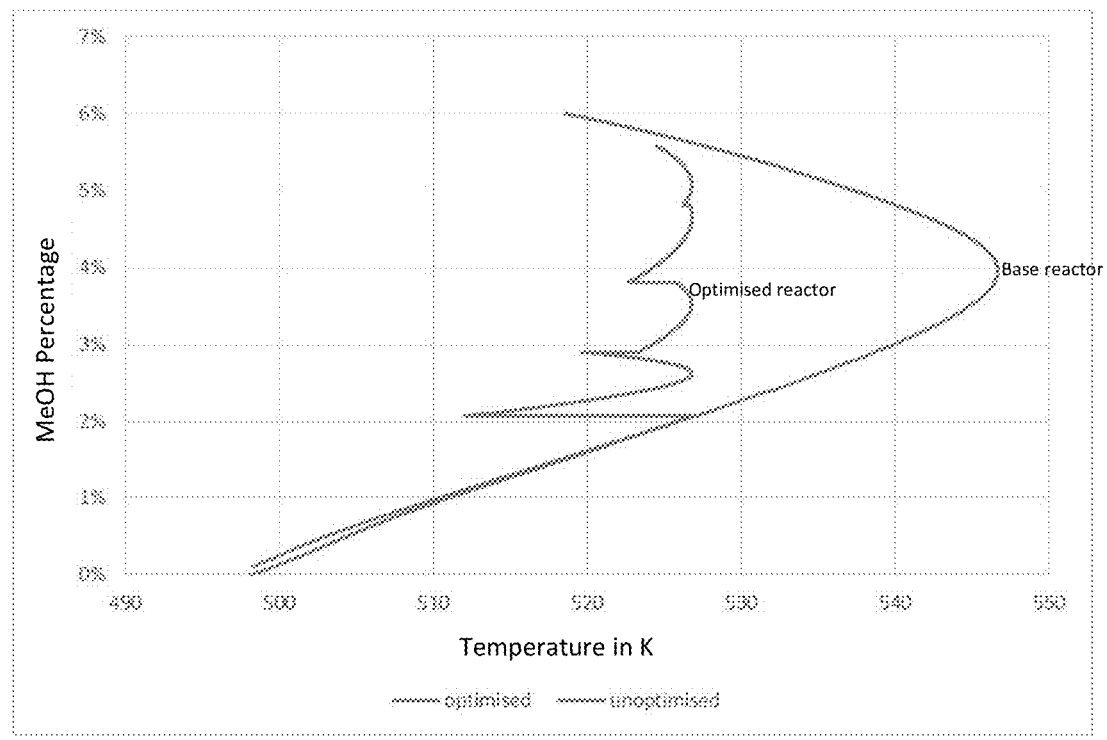
FIG. 19(a) is a graph comparing modelling data for temperature in reactors with and without optimisation of splitting and catalyst area.
Figure 19B:
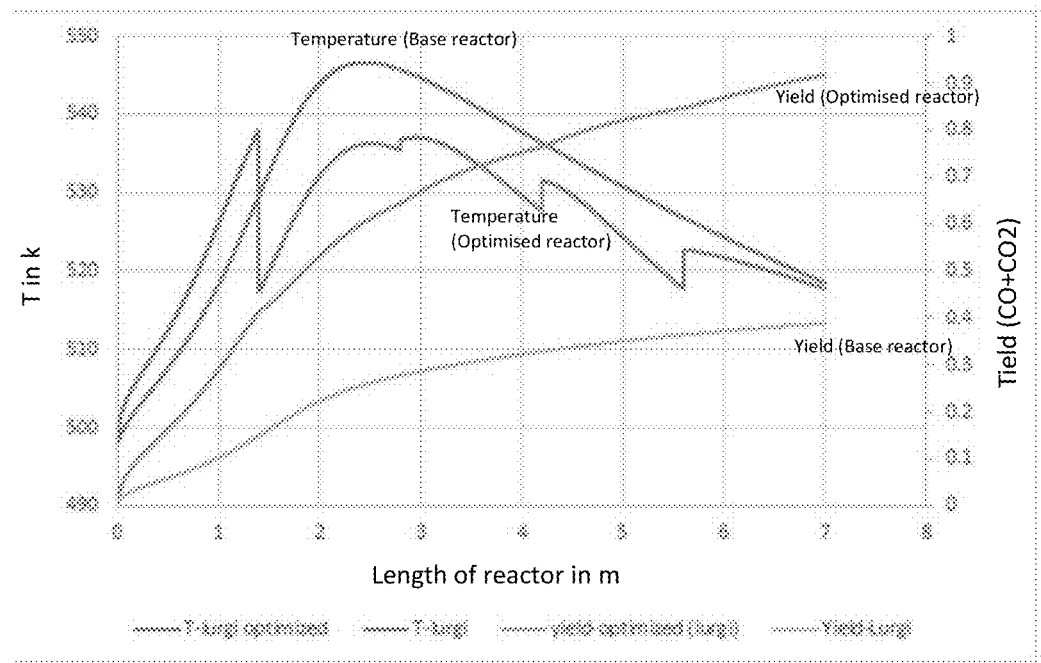
FIG. 19(b) is a graph comparing modelling data for temperature and methanol yield in reactors with and without optimisation of splitting and catalyst area.

An optimisation algorithm was then run to determine the optimised splitting ratio and catalyst area for each stage. A comparison of the performance of a base Lurgi reactor and the Lurgi reactor with optimised splitting ratio and catalyst area are shown in FIGS. 19(a) and 19(b), showing greatly improved temperature profile and methanol yield in the optimised reactor.

Without wishing to be bound by theory, it is believed that the observed improvements are primarily attributable to the improved heat distribution along the length of the reactor and optimised partial pressures of the reactant.

Figure 20:
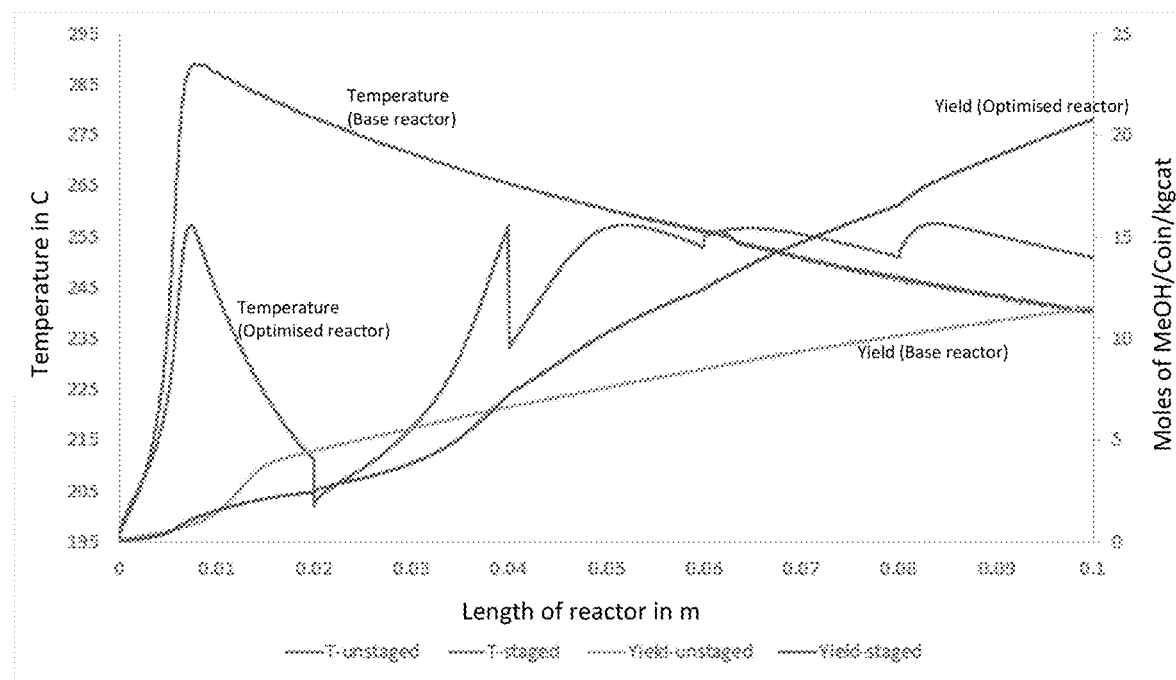
FIG. 20 is a graph showing comparing experimental data for a lab-scale reactor with and without optimisation of splitting and catalyst area.

Lab-scale testing was also conducted to validate the findings of the above modelling. Referring to FIG. 20, it can be seen that in the reactor with optimised split ratios and catalyst area per stage, the peak temperature of the reactor was reduced and methanol yield increased.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A reactor for thermochemical reactions, comprising:
   a reactor shell having an inlet for receiving reactants into the reactor and an outlet for the removal of products from the reactor;
   a plurality of reaction zones located within the reactor shell comprising a solid catalyst in which at least a portion of the reactants undergo a thermochemical reaction and form a reaction mixture of products and reactants;
   a plurality of heat exchange zones comprising a heat exchange medium;

a plurality of tubes for housing the heat exchange medium, wherein heat is exchanged between the reaction zones and the heat exchange medium through walls of the tubes; and one or more hollow inserts at least partially extending through one or more reaction zones thereby to displace solid catalyst in the reaction zone and reduce temperature variation across the reaction zone, each hollow insert comprising an inlet and an outlet, the hollow inserts configured to:

form a flow path to divert a portion of the reactants or reaction mixture from the reactor inlet or from one reaction zone to a different reaction zone.

2. A reactor according to claim 1, wherein the flow path is defined by at least one longitudinally extending bore in the hollow insert.

3. A reactor according to claim 2, wherein the flow path is further defined by at least one laterally extending bore in fluid communication with the at least one longitudinally extending bore.

4. A reactor according to claim 1, wherein the hollow inserts comprise an assembly of hollow insert portions which, when assembled, define a longitudinally extending passage with one or more laterally extending passages.

5. The reactor according to claim 1, wherein the density or number of inserts is substantially constant across each cross-sectional quadrant around a longitudinal axis of the reactor.

6. The reactor according to claim 5, wherein the one or more inserts are spaced substantially equidistant from adjacent heat exchange zones.

7. The reactor according to claim 1, wherein the inserts are disposed in a symmetrical arrangement relative to a longitudinal axis.

8. A reactor according to claim 1, further comprising one or more wall inserts mounted on an inner wall of the reactor shell.

9. A reactor according to claim 1, wherein the inserts are thermally conductive, said thermal conductivity greater than the thermal conductivity of the solid catalyst.

10. The reactor according to claim 1, wherein the different reaction zone is downstream from the hollow insert inlet.

11. The reactor according to claim 1, wherein at least one insert is connected to one or more tubes with a web member.

12. A reactor according to claim 1, further comprising one or more reaction-free zones disposed between sequential reaction zones.

13. A reactor according to claim 1, wherein the tubes are longitudinally extending tubes.

14. A reactor according to claim 1, wherein the heat exchange medium flows through the reactor in a counter-current or co-current direction to a flow of the reactants.

15. A reactor according to claim 1, wherein the thermochemical reaction is:

the production of methanol from synthesis gas;
the production Fischer Tropsch products from synthesis gas;
the methanation of $CO_x$ reactants;
the production of dimethyl ether (DME) from synthesis gas;
the production of ammonia;
hydrogenation reactions; or
hydrocarbon reforming processes.

16. A method of designing a reactor comprising the steps of:

A. generating a thermochemical reactor model for a reactor according to claim 1;
B. portioning the reactor into one or more virtual reaction zones along a longitudinal axis of the reactor;
C. using the reactor model to determine an expected temperature across each of the virtual reaction zones $Tvr_i$ to compare against a target temperature $T_{target}$;
D. adjusting one or more of the following parameters:
 i. the number, diameter, length and/or positioning of the one or more inserts;
 ii. the inlet point and the outlet point of the one or more inserts;
 iii. the amount of catalyst per unit volume of the reactor;
 iv. the location of the catalyst with respect of the heat exchange zone, hollow inserts and/or inserts; and/or
 v. space velocity of a reactant/reaction mixture within the reactor to thereby meet or approach the criteria of $Tvr_i$ to equal $T_{target}$;
E. repeating step D until said criteria is satisfied.

17. A method of reducing temperature variation across one or more reaction zones in a reactor for thermochemical reactions, wherein said reactor comprises:
a reactor shell having an inlet for receiving reactants into the reactor and an outlet for the removal of products from the reactor;
a plurality of reaction zones comprising a solid catalyst in which at least a portion of the reactants undergo a thermochemical reaction;
a plurality of heat exchange zones located within the reactor shell comprising a heat exchange medium; and
a plurality of tubes for housing or the heat exchange medium, wherein heat is exchanged between the reaction zones and the heat exchange medium through walls of the tubes, the method comprising:
introducing one or more hollow inserts at least partially extending through one or more reaction zones thereby to displace solid catalyst in the reaction zone and reduce temperature variation across the reaction zone, each hollow insert comprising an inlet and an outlet, the hollow inserts configured to:
form a flow path to divert a portion of the reactants or reaction mixture from the reactor inlet or from one reaction zone to a different reaction zone.

* * * * *